(12) United States Patent
Johnston

(10) Patent No.: US 11,971,410 B2
(45) Date of Patent: Apr. 30, 2024

(54) METHODS OF CLASSIFYING RESPONSE TO IMMUNOTHERAPY FOR CANCER

(71) Applicant: Arizona Board of Regents on behalf of Arizona State University, Scottsdale, AZ (US)

(72) Inventor: Stephen Johnston, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 17/651,235

(22) Filed: Feb. 15, 2022

(65) Prior Publication Data

US 2022/0170935 A1 Jun. 2, 2022

Related U.S. Application Data

(62) Division of application No. 16/647,434, filed as application No. PCT/US2018/050827 on Sep. 13, 2018.

(60) Provisional application No. 62/559,337, filed on Sep. 15, 2017.

(51) Int. Cl.
| | | |
|---|---|---|
| *G01N 31/00* | (2006.01) | |
| *C07K 16/28* | (2006.01) | |
| *G01N 33/53* | (2006.01) | |
| *G01N 33/543* | (2006.01) | |
| *G01N 33/574* | (2006.01) | |
| *G16B 40/00* | (2019.01) | |
| *G16H 10/40* | (2018.01) | |
| *G16H 20/00* | (2018.01) | |
| *G16H 50/00* | (2018.01) | |
| *G16H 50/20* | (2018.01) | |
| *G16H 50/30* | (2018.01) | |
| *G16H 50/70* | (2018.01) | |
| *C07K 14/705* | (2006.01) | |
| *G16H 10/60* | (2018.01) | |

(52) U.S. Cl.
CPC ....... *G01N 33/574* (2013.01); *C07K 16/2818* (2013.01); *C07K 16/2827* (2013.01); *G01N 33/543* (2013.01); *G16B 40/00* (2019.02); *G16H 10/40* (2018.01); *G16H 20/00* (2018.01); *G16H 50/00* (2018.01); *G16H 50/20* (2018.01); *G16H 50/30* (2018.01); *G16H 50/70* (2018.01); *C07K 14/70503* (2013.01); *C07K 14/70521* (2013.01); *C07K 16/2803* (2013.01); *C07K 2317/76* (2013.01); *G01N 2800/52* (2013.01); *G01N 2800/60* (2013.01); *G16H 10/60* (2018.01)

(58) Field of Classification Search
None
See application file for complete search history.

(56) References Cited

U.S. PATENT DOCUMENTS

| | | |
|---|---|---|
| 4,342,566 A | 8/1982 | Theofilopoulos et al. |
| 4,444,487 A | 4/1984 | Miller et al. |
| 4,683,195 A | 7/1987 | Mullis et al. |
| 4,704,692 A | 11/1987 | Ladner |
| 4,745,055 A | 5/1988 | Schenk et al. |
| 4,816,567 A | 3/1989 | Cabilly et al. |
| 4,863,457 A | 9/1989 | Lee |
| 4,868,116 A | 9/1989 | Morgan et al. |
| 4,897,355 A | 1/1990 | Eppstein et al. |
| 4,980,286 A | 12/1990 | Morgan et al. |
| 5,084,824 A | 1/1992 | Lam et al. |
| 5,143,854 A | 9/1992 | Pirrung et al. |
| 5,288,514 A | 2/1994 | Ellman |
| 5,378,475 A | 1/1995 | Smith et al. |
| 5,424,186 A | 6/1995 | Fodor et al. |
| 5,443,505 A | 8/1995 | Wong et al. |
| 5,449,754 A | 9/1995 | Nishioka |
| 5,506,337 A | 4/1996 | Summerton et al. |
| 5,539,083 A | 7/1996 | Cook et al. |
| 5,545,568 A | 8/1996 | Ellman |
| 5,556,762 A | 9/1996 | Pinilla et al. |
| 5,565,324 A | 10/1996 | Still et al. |
| 5,565,332 A | 10/1996 | Hoogenboom et al. |
| 5,571,639 A | 11/1996 | Hubbell et al. |
| 5,573,905 A | 11/1996 | Lerner et al. |
| 5,593,839 A | 1/1997 | Hubbell et al. |
| 5,595,915 A | 1/1997 | Geysen |
| 5,596,079 A | 1/1997 | Smith et al. |
| 5,599,695 A | 2/1997 | Pease et al. |
| 5,601,989 A | 2/1997 | Cheever et al. |

(Continued)

FOREIGN PATENT DOCUMENTS

| | | |
|---|---|---|
| CA | 2486738 | 12/2003 |
| CN | 1438324 A | 8/2003 |

(Continued)

OTHER PUBLICATIONS

Gnjatic et al. Journal for ImmunoTherapy of Cancer, published May 16, 2017, vol. 5, Issue 44, pp. 1-18) (Year: 2017).*
Turajlic et al. (Lancet, vol. 18, Issue 8, pp. 1009-1021, Aug. 1, 2017, Published online Jul. 7, 2017) (Year: 2017).*
Alpert et al., A clinically meaningful metric of immune age derived from high-dimensional longitudinal monitoring. Nature Med. Mar. 2019;25(3):487-495.
Fodor et al., Light-directed, spatially addressable parallel—Chemical Synthesis. Science Feb. 1991. 15;251(4995):767-773.
Johnston et al., A New Source of Neoantigens for Pediatric and Adult Brain Cancer Vaccines. Neuro-Oncology, Nov. 11, 2019, 21(6): Abstract ATIM-02, 1 page.

(Continued)

*Primary Examiner* — Lisa V Cook

(74) *Attorney, Agent, or Firm* — Knobbe, Martens, Olson & Bear, LLP

(57) ABSTRACT

Provided herein are methods for classifying how a subject having a cancer will respond to immunotherapeutic (IT) therapy based on the subject's immunosignature or frameshift signature. Also provided herein are methods for classifying a subject having a cancer as having a good prognosis or a poor prognosis based on the subject's immunosignature or frameshift signature.

19 Claims, 17 Drawing Sheets

(56) References Cited

U.S. PATENT DOCUMENTS

| | | |
|---|---|---|
| 5,618,825 A | 4/1997 | Baldwin et al. |
| 5,619,680 A | 4/1997 | Berkovich et al. |
| 5,627,210 A | 5/1997 | Valerio et al. |
| 5,646,285 A | 7/1997 | Baindur et al. |
| 5,663,046 A | 9/1997 | Baldwin et al. |
| 5,670,326 A | 9/1997 | Beutel |
| 5,677,195 A | 10/1997 | Winkler et al. |
| 5,683,899 A | 11/1997 | Stuart |
| 5,686,247 A | 11/1997 | Holland et al. |
| 5,688,696 A | 11/1997 | Lebl |
| 5,688,997 A | 11/1997 | Baldwin et al. |
| 5,698,685 A | 12/1997 | Summerton et al. |
| 5,712,146 A | 1/1998 | Khosla et al. |
| 5,721,099 A | 2/1998 | Still et al. |
| 5,721,367 A | 2/1998 | Kay et al. |
| 5,723,598 A | 3/1998 | Lerner et al. |
| 5,741,713 A | 4/1998 | Brown et al. |
| 5,759,774 A | 6/1998 | Hackett et al. |
| 5,792,431 A | 8/1998 | Moore et al. |
| 5,804,440 A | 9/1998 | Burton et al. |
| 5,807,683 A | 9/1998 | Brenner |
| 5,807,754 A | 9/1998 | Zambias et al. |
| 5,821,130 A | 10/1998 | Baldwin et al. |
| 5,824,520 A | 10/1998 | Mulligan-Kehoe |
| 5,831,014 A | 11/1998 | Cook et al. |
| 5,834,195 A | 11/1998 | Benkovic et al. |
| 5,834,318 A | 11/1998 | Buettner |
| 5,834,588 A | 11/1998 | Wasserman et al. |
| 5,837,243 A | 11/1998 | Deo et al. |
| 5,840,500 A | 11/1998 | Pei et al. |
| 5,840,839 A | 11/1998 | Wang et al. |
| 5,847,150 A | 12/1998 | Dorwald |
| 5,856,107 A | 1/1999 | Ostresh et al. |
| 5,856,496 A | 1/1999 | Fagnola et al. |
| 5,859,190 A | 1/1999 | Meyer et al. |
| 5,864,010 A | 1/1999 | Cook et al. |
| 5,874,443 A | 2/1999 | Kiely et al. |
| 5,877,214 A | 3/1999 | Kim |
| 5,880,972 A | 3/1999 | Horlbeck |
| 5,886,126 A | 3/1999 | Newkome et al. |
| 5,886,127 A | 3/1999 | Newkome et al. |
| 5,891,737 A | 4/1999 | Baindur et al. |
| 5,916,899 A | 6/1999 | Kiely et al. |
| 5,919,523 A | 7/1999 | Sundberg et al. |
| 5,919,955 A | 7/1999 | Fancelli et al. |
| 5,925,527 A | 7/1999 | Hayes et al. |
| 5,939,268 A | 8/1999 | Boger |
| 5,939,598 A | 8/1999 | Kucherlapati et al. |
| 5,942,387 A | 8/1999 | Hollinshead |
| 5,945,070 A | 8/1999 | Kath et al. |
| 5,948,696 A | 9/1999 | Dolle, III et al. |
| 5,958,702 A | 9/1999 | Benner |
| 5,958,792 A | 9/1999 | Desai et al. |
| 5,961,978 A | 10/1999 | Gaudernack et al. |
| 5,962,337 A | 10/1999 | Ohlmeyer |
| 5,965,719 A | 10/1999 | Hindsgaul |
| 5,972,719 A | 10/1999 | Dolle, III et al. |
| 5,976,894 A | 11/1999 | Dolle, III et al. |
| 5,980,704 A | 11/1999 | Cherukuri et al. |
| 5,985,356 A | 11/1999 | Shultz et al. |
| 5,999,086 A | 12/1999 | Ecker |
| 6,001,579 A | 12/1999 | Still et al. |
| 6,004,617 A | 12/1999 | Schultz et al. |
| 6,008,321 A | 12/1999 | Li et al. |
| 6,017,768 A | 1/2000 | Baldwin et al. |
| 6,025,371 A | 2/2000 | Gordeev et al. |
| 6,030,917 A | 2/2000 | Weinberg et al. |
| 6,031,071 A | 2/2000 | Mandeville et al. |
| 6,040,193 A | 3/2000 | Winkler et al. |
| 6,045,671 A | 4/2000 | Wu et al. |
| 6,045,755 A | 4/2000 | Lebl et al. |
| 6,060,596 A | 5/2000 | Lerner et al. |
| 6,061,636 A | 5/2000 | Horlbeck |
| 6,083,763 A | 7/2000 | Balch et al. |
| 6,096,551 A | 8/2000 | Barbas et al. |
| 6,130,364 A | 10/2000 | Jakobovits et al. |
| 6,180,377 B1 | 1/2001 | Morgan et al. |
| 6,261,834 B1 | 7/2001 | Srivastava |
| 6,309,831 B1 | 10/2001 | Goldberg et al. |
| 6,329,209 B1 | 12/2001 | Wagner et al. |
| 6,346,413 B1 | 2/2002 | Fodor et al. |
| 6,346,423 B1 | 2/2002 | Schembri |
| 6,359,125 B1 | 3/2002 | Kim et al. |
| 6,387,631 B1 | 3/2002 | Arnold et al. |
| 6,365,418 B1 | 4/2002 | Wagner et al. |
| 6,399,365 B2 | 6/2002 | Besemer et al. |
| 6,465,183 B2 | 10/2002 | Wolber |
| 6,475,808 B1 | 11/2002 | Wagner et al. |
| 6,475,809 B1 | 11/2002 | Wagner et al. |
| 6,489,159 B1 | 12/2002 | Chenchik et al. |
| 6,496,309 B1 | 12/2002 | Bliton et al. |
| 6,506,558 B1 | 1/2003 | Fodor et al. |
| 6,511,277 B1 | 1/2003 | Norris et al. |
| 6,545,748 B1 | 4/2003 | Trozera |
| 6,567,163 B1 | 5/2003 | Sandstrom |
| 6,569,671 B1 | 5/2003 | Okamoto et al. |
| 6,573,369 B2 | 6/2003 | Henderson et al. |
| 6,604,902 B2 | 8/2003 | Norris et al. |
| 6,620,584 B1 | 9/2003 | Chee et al. |
| 6,630,358 B1 | 10/2003 | Wagner et al. |
| 6,660,479 B2 | 12/2003 | Kim et al. |
| 6,706,875 B1 | 3/2004 | Goldberg et al. |
| 6,723,517 B1 | 4/2004 | Bamdad et al. |
| 6,733,977 B2 | 5/2004 | Besemer et al. |
| 6,759,046 B1 | 7/2004 | Gaudernack et al. |
| 6,780,582 B1 | 8/2004 | Wagner et al. |
| 6,806,954 B2 | 10/2004 | Sandstrom |
| 6,824,669 B1 | 11/2004 | Li et al. |
| 6,861,057 B2 | 3/2005 | Gaudernack et al. |
| 6,877,665 B2 | 4/2005 | Challa et al. |
| 6,890,760 B1 | 5/2005 | Webb |
| 6,897,073 B2 | 5/2005 | Wagner et al. |
| 6,919,181 B2 | 7/2005 | Hargreaves |
| 6,989,267 B2 | 1/2006 | Kim et al. |
| 6,989,276 B2 | 1/2006 | Thompson et al. |
| 7,006,680 B2 | 2/2006 | Gulati |
| 7,078,416 B2 | 7/2006 | Gaudernack et al. |
| 7,081,954 B2 | 7/2006 | Sandstrom |
| 7,108,472 B2 | 9/2006 | Norris et al. |
| 7,130,458 B2 | 10/2006 | Bartell |
| 7,148,058 B2 | 12/2006 | Charych et al. |
| 7,192,927 B2 | 3/2007 | Gaudernack et al. |
| 7,247,469 B2 | 7/2007 | Wagner et al. |
| 7,250,252 B2 | 7/2007 | Katz et al. |
| 7,354,721 B2 | 4/2008 | Tchaga |
| 7,375,117 B2 | 5/2008 | Gaudernack et al. |
| 7,466,851 B2 | 12/2008 | Gulati |
| 7,522,271 B2 | 4/2009 | Sandstrom |
| 7,534,563 B2 | 5/2009 | Hargreaves |
| 7,569,343 B2 | 8/2009 | Marton et al. |
| 7,588,906 B2 | 9/2009 | Brueggemeier et al. |
| 7,622,295 B2 | 11/2009 | Cabezas |
| 7,682,797 B2 | 3/2010 | Thompson et al. |
| 7,682,798 B2 | 3/2010 | Thompson et al. |
| 7,695,919 B2 | 4/2010 | Apel et al. |
| 7,723,125 B2 | 5/2010 | Tchaga |
| 7,794,723 B2 | 9/2010 | Gaudernack et al. |
| 7,863,244 B2 | 1/2011 | Gaudernack et al. |
| 7,993,583 B2 | 8/2011 | Dugan et al. |
| 8,053,552 B2 | 11/2011 | von Knebel-Doeberitz et al. |
| 8,073,626 B2 | 12/2011 | Troup et al. |
| 8,148,141 B2 | 4/2012 | Nokihara et al. |
| 8,193,326 B2 | 6/2012 | Gaudernack et al. |
| 8,242,058 B2 | 8/2012 | Raines et al. |
| RE44,031 E | 2/2013 | Apel et al. |
| 8,481,679 B2 | 7/2013 | Johnston et al. |
| RE44,539 E | 10/2013 | Thompson et al. |
| 8,614,177 B2 | 12/2013 | Gaudernack et al. |
| 8,796,414 B2 | 8/2014 | Johnston et al. |
| 8,821,864 B2 | 9/2014 | von Knebel-Doeberitz et al. |
| 9,115,402 B2 | 8/2015 | Hacohen et al. |
| 9,205,140 B2 | 12/2015 | Kloor et al. |
| 9,254,311 B2 | 2/2016 | Bancel et al. |
| 9,265,816 B2 | 2/2016 | Scheinberg et al. |

(56) References Cited

U.S. PATENT DOCUMENTS

| | | | |
|---|---|---|---|
| 9,284,349 B2 | 3/2016 | Tsunoda et al. | |
| 9,309,298 B2 | 4/2016 | Johnston et al. | |
| 9,340,830 B2 | 5/2016 | Downing et al. | |
| 9,482,666 B2 | 11/2016 | Domenyuk et al. | |
| 9,709,558 B2 | 7/2017 | Johnston et al. | |
| 9,732,131 B2 | 8/2017 | Johnston | |
| 9,757,472 B2 | 9/2017 | Diehnelt et al. | |
| 9,766,239 B2 | 9/2017 | Gupta et al. | |
| 9,863,938 B2 | 1/2018 | Johnston et al. | |
| 9,970,932 B2 | 5/2018 | Woodbury et al. | |
| 10,006,919 B2 | 6/2018 | Woodbury et al. | |
| 10,011,649 B2 | 7/2018 | Diehnelt et al. | |
| 10,046,293 B2 | 8/2018 | Woodbury et al. | |
| 10,125,167 B2 | 11/2018 | Diehnelt et al. | |
| 10,126,300 B2 | 11/2018 | Johnston et al. | |
| 10,416,174 B1 | 9/2019 | Johnston et al. | |
| 10,578,623 B2 | 3/2020 | Woodbury et al. | |
| 10,712,342 B2 | 7/2020 | Johnston et al. | |
| 10,900,975 B2 | 1/2021 | Johnston et al. | |
| 11,168,121 B2 | 11/2021 | Johnston et al. | |
| 11,484,581 B2 | 11/2022 | Johnston et al. | |
| 2002/0052308 A1 | 5/2002 | Rosen et al. | |
| 2003/0082579 A1 | 5/2003 | Felgner et al. | |
| 2003/0207467 A1 | 11/2003 | Snyder et al. | |
| 2004/0038307 A1 | 2/2004 | Lee et al. | |
| 2004/0038556 A1 | 2/2004 | French et al. | |
| 2004/0048311 A1 | 3/2004 | Ault-Riche et al. | |
| 2004/0063902 A1 | 4/2004 | Miranda | |
| 2004/0071705 A1 | 4/2004 | Sato et al. | |
| 2004/0265803 A1 | 12/2004 | von Knebel-Doeberitz et al. | |
| 2005/0009204 A1 | 1/2005 | Fang et al. | |
| 2005/0048566 A1 | 3/2005 | Delisi et al. | |
| 2005/0064395 A1 | 3/2005 | Israel et al. | |
| 2005/0239070 A1 | 10/2005 | Von Knebel-Doeberitz et al. | |
| 2005/0244421 A1 | 11/2005 | Strittmatter et al. | |
| 2005/0255491 A1 | 11/2005 | Lee et al. | |
| 2006/0052948 A1 | 3/2006 | Gorlach | |
| 2007/0003954 A1 | 1/2007 | Kodadek | |
| 2007/0015172 A1 | 1/2007 | Zhang et al. | |
| 2007/0020678 A1 | 1/2007 | Ault-Riche et al. | |
| 2007/0099256 A1 | 5/2007 | Sundararajan et al. | |
| 2007/0122841 A1 | 5/2007 | Rajasekaran et al. | |
| 2007/0248985 A1 | 10/2007 | Dutta et al. | |
| 2008/0026485 A1 | 1/2008 | Hueber et al. | |
| 2008/0124719 A1 | 5/2008 | Chung et al. | |
| 2008/0188618 A1 | 8/2008 | Greving et al. | |
| 2008/0193965 A1 | 8/2008 | Zeng et al. | |
| 2008/0207483 A1 | 8/2008 | Volinia | |
| 2009/0062148 A1 | 3/2009 | Goldberg et al. | |
| 2009/0075828 A1 | 3/2009 | Fisher et al. | |
| 2009/0131278 A1 | 5/2009 | Wagner et al. | |
| 2009/0176664 A1 | 7/2009 | Chu | |
| 2009/0186042 A1 | 7/2009 | Johnston et al. | |
| 2009/0270480 A1 | 10/2009 | Amegadzie et al. | |
| 2010/0034807 A1 | 2/2010 | Moyle | |
| 2010/0035765 A1 | 2/2010 | Kodadek | |
| 2010/0093554 A1 | 4/2010 | Chu | |
| 2010/0111993 A1 | 5/2010 | Tuereci et al. | |
| 2010/0210478 A1 | 8/2010 | Gao et al. | |
| 2010/0261205 A1 | 10/2010 | Kakuta et al. | |
| 2011/0046015 A1 | 2/2011 | Honda et al. | |
| 2011/0065594 A1 | 3/2011 | Thompson et al. | |
| 2011/0071043 A1 | 3/2011 | Sampson et al. | |
| 2011/0105366 A1 | 5/2011 | Lebl et al. | |
| 2011/0105721 A1 | 5/2011 | Gaudernack et al. | |
| 2011/0143953 A1 | 6/2011 | Johnston et al. | |
| 2011/0159530 A1 | 6/2011 | Pass et al. | |
| 2011/0189082 A1 | 8/2011 | Kirchner et al. | |
| 2011/0190149 A1 | 8/2011 | Tainsky et al. | |
| 2011/0229448 A1 | 9/2011 | Kelleher et al. | |
| 2011/0263459 A1 | 10/2011 | Borer et al. | |
| 2011/0275537 A1 | 11/2011 | Rychlewski et al. | |
| 2011/0301057 A1 | 12/2011 | Propheter et al. | |
| 2011/0301058 A1 | 12/2011 | Cheng et al. | |
| 2011/0318380 A1 | 12/2011 | Brix et al. | |
| 2012/0021967 A1 | 1/2012 | Johnston et al. | |
| 2012/0052066 A1 | 3/2012 | Calderon et al. | |
| 2012/0065123 A1 | 3/2012 | Johnston et al. | |
| 2012/0094271 A1 | 4/2012 | Fu et al. | |
| 2012/0189702 A1 | 7/2012 | Gupta et al. | |
| 2012/0190574 A1 | 7/2012 | Johnston et al. | |
| 2012/0238477 A1 | 9/2012 | Albert et al. | |
| 2013/0164856 A1 | 6/2013 | Jebrail et al. | |
| 2013/0224730 A1 | 8/2013 | Johnston et al. | |
| 2013/0236490 A1 | 9/2013 | Kalyanasundaram | |
| 2013/0273002 A1 | 10/2013 | Tuohy | |
| 2014/0087963 A1* | 3/2014 | Johnston | B82Y 15/00 506/18 |
| 2014/0113286 A1 | 4/2014 | Chan et al. | |
| 2014/0128280 A1 | 5/2014 | Johnston et al. | |
| 2014/0170178 A1* | 6/2014 | Kloor | A61K 39/0011 424/277.1 |
| 2015/0079119 A1 | 3/2015 | Johnston | |
| 2015/0217258 A1 | 8/2015 | Woodbury et al. | |
| 2015/0241420 A1 | 8/2015 | Johnston et al. | |
| 2015/0352201 A1 | 12/2015 | Scheinberg et al. | |
| 2016/0038579 A1 | 2/2016 | Kloor et al. | |
| 2016/0041158 A1 | 2/2016 | Woodbury et al. | |
| 2016/0051654 A1 | 2/2016 | Singh et al. | |
| 2016/0051657 A1 | 2/2016 | Varga et al. | |
| 2016/0069895 A1 | 3/2016 | Delamarre et al. | |
| 2016/0101170 A1 | 4/2016 | Hacohen et al. | |
| 2017/0088844 A1 | 3/2017 | Williams | |
| 2017/0121776 A1 | 5/2017 | Soliman et al. | |
| 2017/0212101 A1 | 7/2017 | Zhu et al. | |
| 2018/0259510 A1 | 9/2018 | Woodbury et al. | |
| 2018/0273641 A1 | 9/2018 | Babb et al. | |
| 2018/0284114 A1 | 10/2018 | Johnston | |
| 2018/0340944 A1 | 11/2018 | Han et al. | |
| 2019/0134593 A1 | 5/2019 | Hall et al. | |
| 2019/0194358 A1 | 6/2019 | Johnston et al. | |
| 2019/0271692 A1 | 9/2019 | Johnston et al. | |
| 2019/0307868 A1 | 10/2019 | Rooney | |
| 2020/0188496 A1 | 6/2020 | Johnston et al. | |
| 2020/0209241 A1 | 7/2020 | Johnston | |
| 2020/0256861 A1 | 8/2020 | Johnston et al. | |
| 2020/0276285 A1 | 9/2020 | Johnston et al. | |
| 2021/0011024 A1 | 1/2021 | Johnston et al. | |
| 2021/0223257 A1 | 7/2021 | Johnston et al. | |
| 2022/0008525 A1 | 1/2022 | Johnston | |
| 2022/0162276 A1 | 5/2022 | Johnston | |
| 2022/0251544 A1 | 8/2022 | Johnston et al. | |
| 2022/0257701 A1 | 8/2022 | Johnston et al. | |
| 2023/0181645 A1 | 6/2023 | Johnston | |
| 2023/0338486 A1 | 10/2023 | Johnston et al. | |
| 2023/0338490 A1 | 10/2023 | Johnston | |

FOREIGN PATENT DOCUMENTS

| | | |
|---|---|---|
| CN | 102099372 A | 6/2011 |
| CN | 104853764 A | 8/2015 |
| EP | 0125023 B1 | 6/1991 |
| EP | 0120694 B1 | 7/1993 |
| EP | 0256654 B1 | 9/1996 |
| EP | 1354895 | 10/2003 |
| EP | 1369126 | 12/2003 |
| EP | 1785726 A1 | 5/2007 |
| EP | 2572725 A1 | 3/2013 |
| WO | WO 1988/003565 | 5/1988 |
| WO | WO 1989/007136 | 8/1989 |
| WO | WO 1990/002806 | 3/1990 |
| WO | WO 1990/015070 | 12/1990 |
| WO | WO 1991/018980 | 12/1991 |
| WO | WO 1993/006121 | 4/1993 |
| WO | WO 1994/029348 | 12/1994 |
| WO | WO 1995/012608 | 5/1995 |
| WO | WO 1995/030642 | 11/1995 |
| WO | WO 1995/032731 | 12/1995 |
| WO | WO 1995/035503 | 12/1995 |
| WO | WO 1997/027329 | 7/1997 |
| WO | WO 1999/058552 | 11/1999 |
| WO | WO 2001/056691 | 8/2001 |
| WO | WO 2002/097051 | 12/2002 |
| WO | WO 2003/019192 | 3/2003 |

(56) References Cited

FOREIGN PATENT DOCUMENTS

| | | |
|---|---|---|
| WO | WO 2003/084467 | 10/2003 |
| WO | WO 2003/087162 | 10/2003 |
| WO | WO 2003/087766 | 10/2003 |
| WO | WO 2004/111075 | 12/2004 |
| WO | WO 2005/076009 | 8/2005 |
| WO | WO 2007/068240 | 6/2007 |
| WO | WO 2007/101227 | 9/2007 |
| WO | WO2007/147141 | 12/2007 |
| WO | WO 2008/048970 | 4/2008 |
| WO | WO 2009/126718 | 10/2009 |
| WO | WO 2010/037395 | 4/2010 |
| WO | WO 2010/043668 | 4/2010 |
| WO | WO 2010/059958 | 5/2010 |
| WO | WO 2010/111299 | 9/2010 |
| WO | WO 2010/148365 | 12/2010 |
| WO | WO 2011/109440 | 9/2011 |
| WO | WO 2011/150168 | 12/2011 |
| WO | WO 2012/055069 | 5/2012 |
| WO | WO 2014/154905 | 10/2014 |
| WO | WO 2015/103037 | 7/2015 |
| WO | WO 2015/171747 | 11/2015 |
| WO | WO 2016/073299 | 5/2016 |
| WO | WO-2016073299 A1 * 5/2016 ............ A61P 35/00 |
| WO | WO 2018/222917 | 12/2018 |
| WO | WO 2018/223093 | 12/2018 |
| WO | WO 2018/223094 | 12/2018 |
| WO | WO 2019/046815 | 3/2019 |
| WO | WO 2019/055618 | 3/2019 |
| WO | WO 2019/143712 | 7/2019 |
| WO | WO 2020/068896 | 4/2020 |
| WO | WO 2020/132275 | 6/2020 |
| WO | WO 2020/163802 | 8/2020 |
| WO | WO 2021/046466 | 3/2021 |

OTHER PUBLICATIONS

Jollymore M., Virus research aims to prevent or reverse immune-system aging. Nova Scotia Health Research Annual Report 2017, pub. Feb. 21, 2018, 2 pages. Retrieved from the internet: http://www.nshealth.ca/news/virus-research-aims-prevent-orreverse-immune-system-aging; Oct. 15, 2019.
Legutki et al., Scalable high-density peptide arrays for comprehensive health monitoring. Nature Commun. Sep. 3, 2014;5(1):4785 in 7 pages.
Moudgil et al., Cytokines in autoimmunity: Role in induction, regulation, and treatment. J Interferon & Cyto Res., Oct. 2, 2011;31(1):695-703.
Peterson et al., Comparison of Personal and Shared Frameshift Neoantigen Vaccines in a Mouse Mammary Cancer Model. BMC Immunol. Dec. 2020;21(1): 1-5.
Shin et al., Automated maskless photolithography system for peptide microarray synthesis on a chip. J Comb Chem. 2010;12(4):463-471.
Stafford et al., Immunosignature system for diagnosis of cancer. PNAS Jul. 29, 2014;111(3):e3072-e3080.
Tolonen et al., Optimized in situ construction of oligomers on an array surface. Nucl Acids Res. Oct. 15, 2002;30(20):e107 in 5 pages.
Mullis et al., Specific Enzymatic Amplification of DNA in vitro: The Polymerase Chain Reaction. Cold Spring Harbor Symp Quant Biol. 1987;51: 263-273.
Pimpin et al., Review on Micro- and Nanolithography Techniques and Their Applications. Engin J. Jan. 1, 2012;16(1): 37-55.
Szymczak et al., Peptide Arrays: Development and Application. Anal Chem. Jan. 1, 2018;90(1): 266-282.
Zhang et al., Peptide Arrays, Microarrays in Diagnostics and Biomarker Development, B. Jordan (Ed.), Springer-Verlag Berlin, Heidelberg; Chapter 7, 2012; pp. 81-112.
Gnjatic, S., et al. Identifying baseline immune-related biomarkers to predict clinical outcome of immunotherapy, Journal of Immunotherapy of Cancer, 2017, 5(44):1-18.
Maletzki, C., et al. Frameshift-derived neoantigens constitute immunotherapeutic targets for patients with rnicrosatellite-instable haematological malignancies: Frameshift peptides for treating MSI+ blood cancers, European Journal of Cancer, 2013, 49(11 ):2587-2595.
Reuschenbach, M., et al. Serum antibodies against frameshift peptides in microsatellite unstable colorectal cancer patients with Lynch syndrome, Familial Cancer, 2010, 9(2):1-14.
Turajlic, et al. Insertion-and-deletion-derived tumour-specific neoantigens and the immunogenic phenotype: a pan-cancer analysis, Lancet Oncol., Aug. 2017; 18(8):1009-1021.
Shi, L., et al., Application of high-throughput protein array in clinical screening for tumor markers, Int J Clin Exp Med, 2016, 9:8529-8535.
International Search Report and Written Opinion, mailing date Jan. 2, 2019, in International Application No. PCT/US2018/050827. (OEE Work Product).
Amor et al., Senolytic CAR T-cells Reverse Senescence-associated Pathologies. Nature. Jul. 2, 2020;583(7814): 127-132.
Bartok et al., Anti-tumor Immunity Induces Aberrant Peptide Presentation in Melanoma. Nature. Feb. 11, 2021;590(7845): 332-337.
Chaib et al., Cellular Senescence and Senolytics: The Path to the Clinic. Nature Med. Aug. 2022;28(8): 1556-1568.
Furman et al., Chronic Inflammation in the Etiology of Disease Across the Life Span. Nature Med. Dec. 2019;25(12): 1822-1832.
Han S., Clinical Vaccine Development. Clinical and Experimental Vaccine Research. Jan. 1, 2015;4(1): 46-53.
Harries L.W., Dysregulated RNA Processing and Metabolism: A New Hallmark of Ageing and Provocation for Cellular Senescence. FEBS J. Mar. 2023;290(5): 1221-1234.
He et al., Senescence in Health and Disease. Cell. Jun. 1, 2017;169(6): 1000-1011.
Kim et al., Comparison of the effect of different immunological adjuvants on the antibody and T-cell response to immunization with MUC1-KLH and GD3-KLH conjugate cancer vaccines. Vaccine. Nov. 12, 1999;18(7-8): 597-603.
Kirkland et al., Cellular Senescence: A Translational Perspective. EBioMedicine. Jul. 1, 2017;21: 21-28.
López-otín et al. Hallmarks of Aging: An Expanding Universe. Cell Jan. 19, 2023;186: 36 pages.
Met et al., Principles of Adoptive T Cell Therapy in Cancer. Semin Immunopathol. Jan. 2019;41(1): 49-58.
Naqvi et al., Long-term Follow-up of Lower Dose Dasatinib (50 mg daily) as Frontline Thrapy in Newly Diagnosed Chronic-phase Chronic Myeloid Leukemia. Cancer. Jan. 1, 2020;126(1): 67-75.
National Institute of Health [NIH] MedlinePlus—"Vaccines", Definition 2022, in 8 pages.by MedlinePlus.
Pollack et al., Tetramer Guided, Cell Sorter Assisted Production of Clinical Grade Autologous NY-ESO-1 Specific CD8+ T cells. J Immunother Cancer. Dec. 2014;2: 1-0.
Rapoport et al., Combination Immunotherapy after ASCT for Multiple Myeloma Using MAGE-A3/Poly-ICLC Immunizations Followed by Adoptive Transfer of Vaccine-Primed and Costimulated Autologous T cells. Clin Cancer Res. Mar. 1, 2014;20(5): 1355-1365.
Shen et al., Production of High-complexity Frameshift Neoantigen Peptide Microarrays. RSC Advances. 2020;10(50): 29675-29681.
Shen et al., Predicting Response and Toxicity to Immune Checkpoint Inhibitors in Lung Cancer Using Antibodies to Frameshift Neoantigens. J Transl Med. May 22, 2023;21(1): 338 in 14 pages.
Suda et al., Senolytic Vaccination Improves Normal and Pathological Age-related Phenotypes and Increases Lifespan in Progeroid Mice. Nature Aging. Dec. 2021;1(12): 1117-1126.
Suvarna et al., Current Overview on the Clinical Update of Bcl-2 Anti-apoptotic Inhibitors for Cancer Therapy. Eur J Pharmacol. Nov. 5, 2019;862: 172655 in 20 pages.
Wang et al., Comprehensive Map of Age-associated Splicing Changes Across Human Tissues and Their Contributions to Age-associated Diseases. Sci Rep. Jul. 19, 2018;8(1): 10929 in 12 pages.
Yang et al., NKG2D-CAR T-cells Eliminate senescent Cells in Aged Mice and Nonhuman Primates. Scie Transl Med. Aug. 16, 2023;15(709): eadd1951 in 15 pages.
Zhong et al., Comparison of the Molecular and Cellular Phenotypes of Common Mouse syngeneic Models with Human Tumors. BMC Genom. Dec. 2020;21: 1-7.

(56) References Cited

OTHER PUBLICATIONS

Zhu et al., The Achilles' Heel of Senescent Cells: From Transcriptome to Senolytic Drugs. Aging Cell. Aug. 2015;14(4): 644-658.
Zhou et al., Translation of Noncoding RNAs and Cancer. Cancer Letts. Jan. 28, 2021;497: 89-99.
Abrahmsén et al., Engineering Subtilisin and Its Substrates for Efficient Ligation of Peptide Bonds in Aqueous Solution. Biochem. Apr. 1991;30(17): 4151-4159.
ACS, Cancer Facts and Figures 2016 Special Section: Cancer in Asian Americans, Native Hawaiians, and Pacific Islanders. American Cancer Society pp. 1-72.
Acsadi et al., Human Dystrophin Expression in MDX Mice After Intramuscular Injection of DNA Constructs. Nature Aug. 1991;352(6338): 815-818.
Almquist et al., Synthesis and Biological Activity of a Ketomethylene Analogue of a Tripeptide Inhibitor of Angiotensin Converting Enzyme. J Med Chem. 1980;23:1392-1398.
Anthony-Cahill et al., Site-Specific Mutagenesis With Unnatural Amino Acids. Trends Biochem Sciences. Oct. 1, 1989;14(10): 400-403.
Arivazhagan et al., MicroRNA-340 Inhibits the Proliferation and Promotes the Apoptosis of Colon Cancer Cells by Modulating REV3L. Oncotarget Dec. 2017;9(4): 5155-5168.
Bae et al., Microsatellite Instability Status is Critical to Analysis of Survival in Stage II Colon Cancer. J Clin Oncol. Feb. 20, 2012;30(6): 675-676.
Baggiolini et al., Interleukin-8, A Chemotactic and Inflammatory Cytokine. FEBS Lett. Jul. 27, 1992;307:97-101.
Bagshawe et al., A Cytotoxic Agent can be Generated Selectively at Cancer Sites. Br J Cancer. Dec. 1988;58(6): 700-703.
Bagshawe K.D., The First Bagshawe Lecture. Towards Generating Cytotoxic Agents at Cancer Sites. Br J Cancer Sep. 1989;60(3): 275-281.
Balboni et al., Multiplexed Protein Array Platforms for Analysis of Autoimmune Diseases. Ann Rev Immunol. Apr. 23, 2006;24: 391-418.
Banerji et al., A Lymphocyte-Specific Cellular Enhancer is Located Downstream of the Joining Region in Immunoglobulin Heavy Chain Genes. Cell. Jul. 1, 1983;33(3): 729-740.
Bauer et al., T Celll Responses Against Microsatellite Instability-Induced Frameshift Peptides and Influence of Regulatory T Cells in Colorectal Cancer. Cancer Immunol Immunother. Jan. 2013;62(1): 27-37.
Bellone et al., Relevance of the Tumor Antigen in the Validation of Three Vaccination Strategies for Melanoma. J Immunol, (2002) 165 (5), 2651-2656.
Benner S.A., Expanding the Genetic Lexicon: Incorporating Non-Standard Amino Acids Into Proteins by Ribosome-Based Synthesis. Trends Biotech. May 1, 1994;12(5): 158-163.
Berkner et al., Abundant Expression of Polyomavirus Middle T Antigen and Dihydrofolate Reductase in an Adenovirus Recombinant. J Virol. Apr. 1987;61(4): 1213-1220.
Berzofsky, J., et al. Progress on new vaccine strategies for the immunotherapy and prevention of cancer. J Clin Invest. (Jun. 2004) 113(11): 1515-1525.
Bock et al., Selection of Single-Stranded DNA Molecules That Bind and Inhibit Human Thrombin. Nature Feb. 1992;355(6360): 564-566.
Boerner et al., Production of Antigen-Specific Human Monoclonal Antibodies from In Vitro-Primed Human Splenocytes. J Immunol., Jul. 1, 1991;147(1): 86-95.
Bonneville et al., Landscape of Microsatellite Instability Across 39 Cancer Types. JCO Precis Oncol. Sep. 2017;1: 1-5.
Borovkov et al., New Classes of Orthopoxvirus Vaccine Candidates by Functionally Screening a Synthetic Library for Protective Antigens. Virol. Dec. 5, 2009;395(1): 97-113.
Bout et al., Lung Gene Therapy: In Vivo Adenovirus-Mediated Gene Transfer to Rhesus Monkey Airway Epithelium. Hum Gene Thera. 1994;5: 3-10.

Bradner et al., Transcriptional Addiction in Cancer. Cell Feb. 9, 2017;168(4): 629-643.
Brown et al., Penetration of Host Cell Membranes by Adenovirus 2. J Virol. Aug. 1973; 12(2): 386-396.
Brown et al., Molecular and Cellular Mechanisms of Receptor-Mediated Endocytosis. DNA Cell Biol. Jul. 1991;10(6): 399-409.
Brüggermann et al., Designer Mice: The Production of Human Antibody Repertoires in Transgenic Animals. Year Immunol. 1993;7: 33-40.
Caillaud et al., Adenoviral Vector as a Gene DElivery System Into Cultured Rat Neuronal and Glial Cells. Eu J Neurosci. Oct. 1993;5(10): 1287-1291.
Chalmers et al., Analysis of 100,000 Human Cancer Genomes Reveals the Landscape of Tumor Mutational Burden. Genome Med. Dec. 2017;9(1): 34 (14 pages).
Chambers et al., High-Level Generation of Polyclonal Antibodies by Genetic Immunization. Nat Biotechnol. Sep. 2003;21(9): 1088-1092.
Chan et al., 5-day dosing schedule of temozolomide in relapsed sensitive or refractory small cell lung cancer (SCLC) and methyl-guanine-DNA methyltransferase (MGMT) analysis in a phase II trial. Journal of Clinical Oncology, 2012 ASCO Annual Meeting Abstracts. (May 20, 2012) 30(15 Suppl) Abstract No. 7052.
Chang et al., Identifying Recurrent Mutations in Cancer Reveals Widespread Lineage Diversity and Mutational Specificity. Nature Biotech. Feb. 2016;34(2): 155-165.
Chen, W. et al. Modification of Cysteine Residues In Vitro and In Vivo Affects the Immunogenicity and Antigenicity of Major Histocompatibility Complex Class I restricted Viral Determinants. J Exp Med., Jun. 7, 1999;189(11): 1757-1764.
Clark-Lewis et al., Chemical Synthesis, Purification, and Characterization of Two Inflammatory Proteins, Neutrophil Activating Peptide 1 (Interleukin-8) and Neutrophil Activating Peptide. Biochem. Mar. 26, 1996;30(12): 3128-3135.
Clark-Lewis et al., Structural Requirements for Interleukin-8 Function Identified by Design of Analogs and CXC Chemokine Hybrids. J Biol Chem. 1994;269: 16075-16081.
ClinicalTrials.gov; Identifier NCT02563002; Study of Pembrolizumab (MK-3475) vs Standard Therapy in Participants with Microsatellite Instability-High (MSI-H) or Mismatch Repair Deficient (dMMR) Stage IV Colorectal Carcinoma (MK-3475-177/KEYNOTE-177), published Sep. 29, 2015; 13 pages.
Cohen et al., An Artificial Cell-Cycle Inhibitor Isolated From a Combinatorial Library. PNAS U.S.A. Nov. 24, 1998;95(24): 14272-14277.
Collura et al., Patients With Colorectal Tumors with Microsatellite Instability and Large Deletions in HSP110 T17 Have Improved Response to 5-Fluorauracil-Based Chemotherapy. Gastroenter. Feb. 1, 2014;146(2): 401-411.
Cramer et al., Conditions Associated With Antibodies Against the Tumor-Associated Antigen MUC1 and Their Relationship to Risk for Ovarian Cancer. Cancer Epidem Biomark Prevent. May 2005;14(5): 1125-1131.
Davidson et al., Overproduction of Polyomavirus Middle T Antigen in Mammalian Cells Through the Use of an Adenovirus Vector. J Virol. Apr. 1987;61(4): 1226- 1239.
Dawson et al. Synthesis of Proteins by Native Chemical Ligation. Science, Nov. 4, 1994;266: 776-779.
Disis et al., HER-2/neu Oncogenic Protein: Issues in Vaccine Development. Crit Rev Immunol., (1998);18(1-2): 37-45.
Donnelly et al., Technical and Regulatory Hurdles for DNA Vaccines. Int J Parasitol. (2003) 33(5-6): 457-467.
Duan H., Early Detection and Treatment of Breast Cancer by Random Peptide Array in neuN Transgenic Mouse Model. Doctoral Thesis; Arizona State University Jun. 30, 2015, 168 pages.
Dudley et al., Microsatellite Instability as a Biomarker for PD-1 Blockade. Clin Cancer Res. Feb. 15, 2016;22(4): 813-820.
Dunn et al., Cancer Immunoediting: From Immunosurveillance to Tumor Escape. Nature Immunol. Nov. 2002;3(11): 991-998.
Ellington et al., In Vitro Selection of RNA Molecules That Bind Specific Ligands. Nature. Aug. 1990;346(6287): 818-822.

(56) References Cited

OTHER PUBLICATIONS

Ellington et al., Selection In Vitro of Single-Stranded DNA Molecules That Fold Into Specific Ligand-Binding Structures. Nature Feb. 1992;355(6363): 850-852.
Emens et al., Toward a Breast Cancer Vaccine: Work in Progress. Oncol. Sep. 1, 2003;17(9): 1217.
Englehard V.H., Structure of Peptides Associated with Class I and Class II MHC Molecules. Annu Rev Immunol. Apr. 1994;12: 181-207.
Falkner et al., Expression of Mouse Immunoglobulin Genes in Monkey Cells. Nature Jul. 15, 1982;298(5871): 286-288.
Felgner et al., Lipofection: A Highly Efficient, Lipid-Mediated DNA-Transfection Procedure. PNAS U.S.A. Nov. 1987;84(21): 7413-7417.
Fidler I.J., Selection of Successive Tumour Lines for Metastasis. Nature New Biol. Apr. 1973;242(118): 148-149.
Fields et al., A novel genetic system to detect protein-protein interactions. Nature Jul. 20, 1989;340(6230): 245-246.
Filley et al., Recurrent Glioma Clinical Trial; CheckMate-143: The Game is not over yet. Oncotarget Oct. 10, 2017;8(53): 91779-91794.
Finn O.J., Cancer Vaccines: Between the Idea and the Reality. Nat Rev Immunol., Aug. 2003;3(8): 630-641.
Finn O.J., Premalignant Lesions as Targets for Cancer Vaccines. J Exp Med. Dec. 1, 2003;198(11): 1623-1626.
Food & Drug Administration (FDA), News Release. FDA Approves first Cancer Treatment for Any Solid Tumor With a Specific Genetic Feature; published online on May 23, 2017; 3 pages.
Food & Drug Administration (FDA), FDA Grants Accelerated Approval to Ipilimumab for MSI-H or dMMR Metastatic Colorectal Cancer. Published Jul. 10, 2018; 2 pages.
Food & Drug Administration (FDA), FDA Grants Nivolumab Accelerated Approval for MSI-H or dMMR Colorectal Cancer. Published Jul. 31, 2017; 2 pages.
Forsstrom et al., Proteome-Wide Epitope Mapping of Antibodies Using Ultra-Dense Peptide Arrays. Mol Cell Proteomics 2014;13:; 1585-1597.
Gao et al., High Density Peptide Microarrays. In Situ Synthesis and Applications. Mol Diversity. Sep. 2004;8(3): 177-187.
Garon et al., Pembrolizumab for the Treatment of Non-Small-Cell Lung Cancer. N Engl J Med. May 21, 2015;372(21): 2018-2028.
Georgiadis et al., Non-Invasive Detection of Microsatellite Instability and High Tumor Mutation Burden in Cancer Patients Treated with PD-1 Blockade. Clin Cancer Res. Dec. 1, 2019;25(23): 7024-7034.
Gite et al. A High-throughput Nonisotopic Protein Truncation Test. Nat Biotech., Feb. 2003;21(2): 194-197.
Goldman et al., The UCSC Cancer Genomics Browser: Update 2015. Nucleic Acids Res. Jan. 28, 2015;43(D1): D812-D817.
Gómez-Foix et al., Adenovirus-Mediated Transfer of the Muscle Glycogen Phosphorylase Gene IntoHepatocytes Confers Altered Regulation of Glycogen Metabolism. J Biol Chem. Dec. 15, 1992;267(35): 25129-25134.
Goodman et al., Tumor Mutational Burden as an Independent Predictor of Response to Immunotherapy in Diverse Cancers. Mo. Cancer Ther. Nov. 1, 2017;16(11): 2598-2608.
Gout et al., Large-Scale Detection of in vivo Transcription Errors. PNAS U S A. Nov. 12, 2013;110(46): 18584-18589.
Gout et al., The Landscape of Transcriptioin Errors in Eukaryotic Cells. Science Adv. Oct. 20, 2017;3(10): e1701484.
Guo et al., Therapeutic Cancer Vaccines: Past, Present and Future. Adv Cancer Res. Jan. 1, 2013;119: 421-475.
Halperin et al., Exploring Antibody Recognition of Sequence Space Through Random-Sequence Peptide Microarrays. Mol Cell Proteo. Nov. 1, 2010;10(3): 10 pages.
Hanahan et al., Hallmarks of Cancer: The Next Generation. Cell Mar. 4, 2011;144(5): 646-674.
Hann et al., On the Double Bond Isostere of the Peptide Bond: Preparation of an Enkephalin Analogue. J Chem Soc Perkin Transl I. 1982; 307-314.
Hansen et al., Polyclonal Antibody Production for Membrane Proteins via Genetic Immunization. Sci Rep. Feb. 24, 2016;6(1): 227 (13 pages).
Hansen et al., Combination of RNA- and Exome Sequencing: Increasing Specificity for Identification of Somatic Point Mutations and Indels in Acute Leukaemia. Leuk Res. Dec. 2016;51: 27-31.
Hause et al., Classification and Characterization of Microsatellite Instability Across 18 Cancer Types. Nat Med Nov. 2016;22(11): 1342-1350.
Hellmann et al. Genomic Profile, Smoking, and Response to Anti-PD-1 Therapy in Nonsmall Cell Lung Carcinoma. Mol Cell Oncol. 20163(1):e1048929 (3 pages) (2016).
Hirayama et al., The Present Status and Future Prospects of Peptide-based Cancer Vaccines. Int Immunol. Jul. 1, 2016;28(7): 319-328.
Hodges et al., Mutational Burden, Immune Checkpoint Expression, and Mismatch Repair in Glioma: Implications for Immune Checkpoint Immunotherapy. Neuro Oncol. Aug. 1, 2017;19(8): 1047-1057.
Holladay et al., Synthesis of Hydroxyethylene and Ketomethylene Dipeptide Isosteres. Tetrahedron Lett. Jan. 1, 1983;24(41): 4401-4404.
Hollingsworth et al., Turning the Corner on Therapeutic Cancer Vaccines. NPJ Vac. Feb. 8, 2019:4(1): 10 pages.
Hoogenboom et al., By-Passing Immunisation: Human Antibodies from Synthetic Repertoires of Germline VH Gene Segments Rearranged In Vitro. J Mol Biol. 1991;227:381-388.
Hruby V.J., Conformational Restrictions of Biologically Active Peptides Via Amino Acid Side Chain Groups. Life Sci. Jul. 19, 1982;31(3): 189-199.
Hughes et al., Monoclonal Antibody Targeting of Liposomes to Mouse Lung In Vivo. Cancer Res. Nov. 15, 1989;49(22): 6214-6220.
Ibba et al., Towards Engineering Proteins by Site-Directed Incorporation In Vivo of Non-Natural Amino Acids. Bio/Tech. Jul. 1994;12(7): 678-682.
Itakura et al., Synthesis and Use of Synthetic Oligonucleotides. Ann Rev Biochem. 1984;53: 323-356.
Imashimizu et al., Direct Assessment of Transcription Fidelity by High-Resolution RNA Sequencing. Nucleic Acids Res. Oct. 1, 2013;41(19): 9090-9104.
Jaeger et al. Improved Predictions of Secondary Structures for RNA. PNAS U.S.A. Oct. 1989;86(20): 7706-7710.
Jaeger et al., Predicting Optimal and Suboptimal Secondary Structure for RNA. Meth Enzymol. 1990;183: 281-306.
Jaffe S., Vax Facts. The Scientist. Mar. 2004; 2 pages.
Jakobovits et al., Analysis of Homozygous Mutant Chimeric Mice: Deletion of the Immunoglobulin Heavy-Chain Joining Region Blocks B-Cell Development and Antibody Production. PNAS U.S.A. Mar. 15, 1993; 90(6): 2551-2555.
Jakobovits et al., Germ-Line Transmission and Expression of a Human-Derived Yeast Artificial Chromosome. Nature Mar. 18, 1993;362(6417): 255-258.
Jennings-White et al., Synthesis of Ketomethylene Analogs of Dipeptides. Tetra Ltt. Jan. 1, 1982;23(25): 2533-2534.
Jones et al., Replacing the Complementarity-Determining Regions in a Human Antibody With Those From a Mouse. Nature 1986;321(6069): 522-525.
Kahles et al., Comprehensive Analysis of Alternative Splicing Across Tumors from 8,705 Patients. Cancer Cell Aug. 13, 2018;34(2): 211-224.
Kandoth et al., Mutational Landscape and Significance Across 12 Major Cancer Types. Nature Oct. 2013;502(7471): 333-339.
Kerr C., Huntington's disease provides cancer clues. The Lancet Oncol. Sep. 1, 2002;3(9): 518.
Keskin et al., Neoantigen Vaccine Generates Intratumoral T Cell Responses in Phase Ib Glioblastoma Trial. Nature Jan. 2019;565(7738): 234-239.
Kimura et al., MUC1 Vaccine for Individuals with Advanced Adenoma of the Colon: A Cancer Immunoprevention Feasibility StudyMUC1 Vaccine Clinical Trial for Colon Cancer Prevention. Cancer Prevent Res. Jan. 1, 2013;6(1): 18-26.

(56) References Cited

OTHER PUBLICATIONS

Kirovski, D. et al. Combinatorics of the Vaccine Design Problem: Definition and an Algorithm.Technical Report MSR-TR-2007-148. Microsoft Research (http://research.microsoft.com); Nov. 2007; 11 pages.

Kirshenbaum et al., Highly Efficient Gene Transfer Into Adult Ventricular Myocytes by Recombinant Adenovirus. J Clin Invest. Jul. 1, 1993;92(1): 381-387.

Kloor et al., The Immune Biology of Microsatellite-Unstable Cancer. CellPress Trends in Cancer Mar. 2016;2(3): 121-133.

Köhler et al., Continuous Cultures of Fused Cells Secreting Antibody of Predefined Specificity. Nature, Aug. 7, 1975;256(5517): 495-497.

König R., Interactions Between MHC Molecules and Co-Receptors of the TCR. Curr Opin Immunol. Feb. 1, 2002;14(1): 75-83.

Korber et al., Immunoinformatics Comes of Age. PLoS Compu Biol. Jun. 2006;2(6):e71 (0484-0492).

Kreiter et al., Mutant MHC Class II Epitopes Drive Therapeutic Immune Responses to Cancer. Nature Apr. 2015;520(7549): 692-696.

Krieg A.M., CpG Motifs: The Active Ingredient in Bacterial Extracts? Nat Med. Jul. 2003;9(7): 831-835.

Larkin et al., Combined Nivolumab and Ipilimumab or Monotheraby in Untreated Melanoma. New Engl J Med. Jul. 2, 2015;373(1): 23-34.

La Salle et al., An Adenovirus Vector For Gene Transfer Into Neurons and Glia in the Brain. Science Feb. 12, 1993;259(5097): 988-990.

Le et al., PD-1 Blockade in Tumors with Mismatch-Repair Deficiency. N Engl J Med Jun. 25, 2015;372(26): 2509-250.

Le et al., Mismatch Repair Deficiency Predicts Response of Solid Tumors to PD-1 Blockade. Science Jul. 28, 2017;357(6349): 409-413.

Leaf C., Why We're Losing the War on Cancer. Fortune. Mar. 22, 2004;149(6): 76-79.

Lee H., Identification of Neo-antigens for a Cancer Vaccine by Transcriptome Analysis. Doctoral Dissertation, Arizona State University, (May 2012), 168 pages.

Lee et al., Transcriptional Regulation and Its Misregulation in Disease. Cell Mar. 14, 2013;152(6): 1237- 1251.

Lee et al., Therapeutic Targeting of Splicing in Cancer. Nat Med. Sep. 2016;22(9): 976-986.

Legutki et al., A General Method for Characterization of Humoral Immunity Induced by a Vaccine or Infection. Vaccine Jun. 17, 2010;28(28): 4529-4537.

Lennerz et al., The Response of Autologous T Cells to a Human Melanoma is Dominated by Mutated Neoantigens. PNAS. Nov. 1, 2005;102(44): 16013-16018.

Letsinger et al., Cholesteryl-Conjugated Oligonucleotides: Synthesis, Properties, and Activity as Inhibitors of Replication of Human Immunodeficiency Virus in Cell Culture. PNAS U.S.A. Sep. 1989; 86(17): 6553-6556.

Lewis J.J., Therapeutic cancer vaccines: using unique antigens. PNAS: (2004) 101 Supplement 2:14653-14656.

Leyssen et al., Prospects for Antiviral Therapy. Adv Virus Res. 61, 511-53 (2003).

Li et al., Preclinical and Clinical Development of Neoantigen Vaccines. Ann Oncol. Dec. 28, 2017;28(12 Suppl): xii11-17.

Lin et al., Evaluation of MHC Class I Peptide Binding Prediction Servers: Application for Vaccine Research. BMC Immunol. Dec. 2008; 9(1): 1-3.

Lin et al., Transcriptional Amplification in Tumor Cells with Elevated c-Myc. Cell Sep. 2012;151(1): 56-67.

Lin et al., DNA Mismatch Repair and p53 Function are Major Determinants of the Rate of Development of Cisplatin Resistance. Mol Cancer Thera. May 2006;5(5): 1239-1247.

Lindahl T., DNA Repair: DNA Surveillance Defect in Cancer Cells. Curr Biol. Mar. 1, 1994;4(3): 249-251.

Linnebacher, M. et al. Frameshift Peptide-Derived T-Cell Epitopes: A Source of Novel Tumor-Specific Antigens. Int J Cancer, Jul. 1, 2001;93(1): 6-11.

Linnemann et al., High-Throughput Epitope Discovery Reveals Frequent Recognition of Neo-Antigens by CD4+ T Cells in Human Melanoma. Nat Med. Jan. 2015;21(1): 81-85.

Lollini et al., Vaccines and Other Immunological Approaches for Cancer Immunoprevention. Curr Drug Targets Dec. 1, 2011;12(13): 1957-1973.

Lusky et al., Bovine Papilloma Virus Contains an Activator of Gene Expression at the Distal End of the Early Transcription Unit. Mol Cell Biol. Jun. 1983;3(6): 1108-1122.

Lykke-Andersen et al., Nonsense-Mediated mRNA Decay: An Intricate Machinery that Shapes Transcriptomes. Nat Rev Mol Cell Biol. 2015;16: 665-677.

Macmillan Publishers Ltd., Misguided Cancer Goal. This Week—Nature Nov. 29, 20129;491: 637.

Maher et al., Transcriptome Sequencing to Detect Gene Fusions in Cancer. Nature Mar. 2009;458(7234): 97-101.

Maher et al., Chimeric Transcript Discovery by Paired-End Transcriptome Sequencing. PNAS U S A. Jul. 28, 2009:106(30): 12353-12358.

Martin et al., Low Mutation Burden in Ovarian Cancer May Limit the Utility of Neoantigen-Targeted Vaccines. Plos One. May 18, 2016;11(5): e0155189 (15 pages).

Massie et al., Construction of a Helper-Free Recombinant Adenovirus That Expresses Polyomavirus Large T Antigen. Mol Cell Biol. Aug. 1986;6(8): 2872-2883.

Minev B.R., Melanoma Vaccines. Semin Oncol. Oct. 1, 2002; 29 (5): 479-493.

Morrison S.L., Sequentially Derived Mutants of the Constant Region of the Heavy Chain of Murine Immunoglobulins. J Immunol. Aug. 1979;123(2): 793-800.

Morrison et al., Chimeric Human Antibody Molecules: Mouse Antigen-binding Domains with Human Constant Region Domains. Proc Natl Acad Sci USA. Nov. 1984;81(21):6851-6855.

Morsy et al., Efficient Adenoviral-Mediated Ornithine Transcarbamylase Expression in Deficient Mouse and Human Hepatocytes. J Clin Invest. Sep. 1, 1993;92(3): 1580-1586.

Motzer et al., Nivolumab Versus Everolimus in Advanced Renal-Cell Carcinoma. N Engl J Med. Nov. 5, 2015;373(19): 1803-1813.

Moullier et al., Adenoviral-Mediated Gene Transfer to Renal Tubular Cells In Vivo. Kidney Internat. Apr. 1, 1994;45(4): 1220-1225.

Mulligan R.C., The Basic Science of Gene Therapy. Science. May 14, 1993;260(5110): 926-932.

Needleman et al., A General Method Applicable to the Search for Similarities in the Amino Acid Sequence of Two Proteins. J Mol Biol. Mar. 1970;48(3): 443-453.

Negrini et al., Genomic Instability—An Evolving Hallmark of Cancer. Nat Rev Mol Cell Biol. Mar. 2010;11(3): 220-228.

Nestle F.O., Vaccines and Melanoma. Clin Exper Dermatol. 27: 597-601 (2002).

Nielsen et al., Peptide Nucleic Acid (PNA). A DNA Mimic With a Peptide Backbone. Biocon Chem. Jan. 1, 1994;5(1): 3-7.

O'Leary et al., Reference Sequence (RefSeq) Database at NCBI: Current Status, Taxonomic Expansion, and Functional Annotation. Nucleic Acids Res. Jan. 4, 2016;44(D1): D733-D745.

Osborne et al., Transcription Control Region Within the Protein-Coding Portion of Adenovirus E1A Genes. Mol Cell Biol. Jul. 1984;4(7): 1293-1305.

Ott et al., An Immunogenic Personal Neoantigen Vaccine for Patients with Melanoma. Nature. Jul. 2017;547(7662): 217-221.

Oxford University, Combination Vaccines and Multiple Vaccinations; (http://vk.ovg.ox.ac.uk/combination-vaccines-and-multiple-vaccinations) Website Accessed Oct. 4, 2013, 1 page.

Pawlik et al., Malignant Melanoma: Current State of Primary and Adjuvant Treatment. Crit Rev Oncol Hematol. Mar. 1, 2003; 45(3): 245-264.

Pearson et al., Improved Tools for Biological Sequence Comparison. PNAS U.S.A.Apr. 1988;85(8): 2444-2448.

Pietanza et al., Phase II Trial of Temozolomide in Patients with Relapsed Sensitive or Refractory Small Cell Lung Cancer, with

(56) References Cited

OTHER PUBLICATIONS

Assessment of Methylguanine-DNA Methyltransferase as a Potential Biomarker. Clin Cancer Res., (Feb. 15, 2012) 18(4): 1138-1145.
Pietersz et al., Antibody Conjugates for the Treatment of Cancer. Immunol Rev. Oct. 1992; 129(1): 57-80.
Presta L.G., Antibody Engineering. Curr Opin Struct Biol. Aug. 1, 1992;2(4): 593-596.
Pruitt et al., The Consensus Coding Sequence (CCDS) Project: Identifying a Common Protein-Coding Gene Set for the Human and Mouse Genomes. Genome Res. Jul. 1, 2009;19(7): 1316-1323.
Ragot et al., Replication-Defective Recombinant Adenovirus Expressing the Epstein-Barr Virus (EBV) Envelope Glycoprotein gp340/220 Induces Protective Immunity Against EBV-Induced Lymphomas in the Cottontop Tamarin. J Gen Virol. Mar. 1, 1993;74(3): 501-507.
Rajarathnam et al., 1H Nmr studies of interleukin 8 analogs: characterization of the domains essential for function. Biochem. May 31, 1994;33(21): 6623-6630.
Ram et al. In Situ Retroviral-Mediated Gene Transfer for the Treatment of Brain Tumors in Rats. Cancer Res. Jan. 1, 1993;53(1): 83-88.
Rammensee et al, Peptides Naturally Presented by MHC Class I Molecules. Immunol Rev. Apr. 1993; 11(1):213-244.
Rammensee et al., Towards Patient-specific Tumor Antigen Selection for Vaccination. Immunol Rev. Oct. 2002;188(1): 164-176.
Rappuoli et al. [Eds.], New Approaches to Vaccine Design, from Vaccine Design Innovative Approaches and Novel Strategedies; (2011) Caister Academic Press; 12 pages.
Renno et al., What's new in the field of cancer vaccines? Cell Mol Life Sci. CMLS Jul. 2003;60(7): 1296-1310.
Reuschenbach et al., A Multiplex Method for the Detection of Serum Antibodies Against in Silico-Predicted Tumor Antigens. Cancer Immunol Immunother. Dec. 2014;63(12): 1251-1259.
Riechmann et al., Reshaping Human Antibodies for Therapy. Nature Mar. 24, 1988;332(6162): 323-327.
Riess et al., Theory Meets Practice for Immune Checkpoint Blockade in Small-Cell Lung Cancer. J Clin Oncol. Nov. 11, 2016;34(31): 3717-3720.
Rizo et al., Constrained Peptides: Models of Bioactive Peptides and Protein Substructures. Ann Rev Biochem. Jul. 1992;61(1): 387-416.
Rizvi et al., Mutational Landscape Determines Sensitivity to PD-1 Blockade in Non-Small Cell Lung Cancer. Science. Apr. 3, 2015;348(6230): 124-128.
Roberts et al., RNA-Peptide Fusions For The In Vitro Selection of Peptides and Proteins. PNAS U.S.A. Nov. 11, 1997;94(23): 12297-12302.
Roessler et al., Adenoviral-Mediated Gene Transfer to Rabbit Synovium In Vivo. J Clin Invest. J Clin Invest. Aug. 1, 1993;92(2): 1085-1092.
Ruggiano et al., ER-Associated Degradation: Protein Quality Control and Beyond. J Cell Biol. Mar. 17, 2014;204(6): 869-879.
Ryan et al., The Current Value of Determining the Mismatch Repair Status of Colorectal Cancer: A Rationale for Routine Testing. Crit Rev. Oncol/Hemat. Aug. 1, 2017;116: 38-57.
Sade-Feldman et al., Resistance to Checkpoint Blockade Therapy Through Inactivation of Antigen Presentation. Nat Commun. Oct. 26, 2017;8(1): 1136 (in 11 pages).
Sæterdal et al., Frameshift-mutation-derived Peptides as Tumor-Specific Antigens in Inherited and Spontaneous Colorectal Cancer. PNAS USA, Nov. 6, 2001;98(23): 13255-13260.
Sahin et al., Personalized RNA Mutanome Vaccines Mobilize Poly-Specific Therapeutic Immunity Against Cancer. Nature Jul. 2017;547(7662): 222-226.
Salipante et al., Microsatellite Instability Detection by Next Generation Sequencing. Clin Chem. Sep. 1, 2014;60(9): 1192-1199.
Schadendorf et al., Pooled Analysis of Long-Term Survival Data from Phase II and Phase III Trials of Ipilimumab in Unresectable or Metastatic Melanoma. J Clin Oncol. Jun. 6, 2015;33(17): 1889-1894.
Schiffman et al., Comparative Oncology: What Dogs and Other Species Can Teach US About Humans with Cancer. Philos Trans R Soc. London B Biol Sci. Jul. 19, 2015;370(1673): 1-13.
Schultze et al., From Cancer Genomics to Cancer Immunotherapy: Toward Second-generation Tumor Antigens. Trends Immunol. Sep. 1, 2001;22(9): 516-553.
Schumacher et al., Neoantigens in Cancer Immunotherapy. Science Apr. 3, 2015;348(6230): 67-74.
Schwanhäusser et al., Global Quantification of Mammalian Gene Expression Control. Nature. May 2011;473(7347): 337-342.
Seth et al., Role of a Low-pH Environment in Adenovirus Enhancement of the Toxicity of a Pseudomonas Exotoxin-Epidermal Growth Factor Conjugate. J Virol. Sep. 1984;51(3): 650-655.
Seth et al., Evidence That the Penton Base of Adenovirus is Involved in Potentiation of Toxicity of Pseudomonas exotoxin Conjugated to Epidermal Growth Factor. Mol Cell Biol. Aug. 1984;4(8): 1528-1533.
Sette et al., The Relationship Between Class I Binding Affinity and Immunogenicity of Potential Cytotoxic T Cell Epitopes. J Immunol. Dec. 15, 1994;153(12): 5586-5592.
Shen L., Investigation of Tumor Frame Shift Antigens for Prophylactic Cancer Vaccine, Cancer Detection and Tumorigenicity. Doctoral Thesis; Arizona State University. Dec. 2012., 256 pages.
Shen et al., RNA Transcription and Splicing Errors as a Source of Cancer Frameshift Neoantigens for Vaccines. Scientific Rep. Oct. 2, 2019;9(1): 13 pages.
Silvera et al., Translational Control in Cancer. Nat Rev Cancer Apr. 2010;10(4): 254-266.
Smart et al., Intron Retention is a Source of Neoepitopes in Cancer. Nat Biotechnol. Nov. 2018;36(11): 1056-1058.
Smith et al., Comparison of Biosequences. Adv Appl Math Dec. 1, 1981;2(4): 482-489.
Snyder et al., Genetics and Immunology: Reinvigorated. Oncolmmunology, Oct. 3, 2015;4(10): e1029705 (2 pages).
Sørensen et al., Significantly Lower Incidence of Cancer Among Patients with Huntington Disease. J Am Cancer Soc. Oct. 1, 1999;86(7): 355-359.
Spatola A.F., Peptide Backbone Modifications: A Structure-Activity Analysis of Peptides Containing Amide Bond Surrogates, Conformational Constraints, and Related Backbone Replacements. Marcel Dekker, New York (Mar. 1983), Chapter 5; in 91 pages.
Spatola et al., Structure-Activity Relationships of Enkephalins Containing Serially Replaced Thiomethylene Amide Bond Surrogates. Life Sci. Apr. 7, 1986;38(14): 1243-1249.
Stafford et al., Microarray technology displays the complexities of the humoral immune response. Exp Rev Mol Diagn. Jan. 1, 2011;11(1): 5-8.
Stafford et al., Physical Characterization of the "Immunosignaturing Effect". Mol Cell Proteo. Apr. 1, 2012;11(4): M111.011593-1 (14 pages).
Stafford et al., Use of Random Peptide Array to Discover Cancer Neo-Antigens for Vaccines and Diagnostics. Cancer Immunol Res. 2015;3(10 Suppl), Abstract PR10.
Sugden et al., A Vector That Replicates as a Plasmid and Can Be Efficiently Selected in B-Lymphoblasts Transformed by Epstein-Barr Virus. Mol Cell Biol. Feb. 1985;5(2): 410-413.
Sussman H.E., Personalized Cancer Vaccine Promises Remission. Drug Discov Today. 2003;8(15): 657-658.
Svarovsky et al., Self-Assembled Micronanoplexes for Improved Biolistic Delivery of Nucleic Acids. Mo Pharm. Dec. 7, 2009;6(6): 1927-1933.
Svensson U., Role of Vesicles During Adenovirus 2 Internalization Into Hela Cells. J Virol. Aug. 1985;55(2): 442-449.
Sykes et al., Genetic Live Vaccines Mimic the Antigenicity But Not Pathogenicity of Live Viruses. DNA Cell Biol. Jul. 1, 1999;18(7): 521-531.
Sykes et al., Linear Expression Elements: A Rapid, in vivo, Method to Screen for Gene Functions. Nat Biotech. Apr. 1999;17(4): 355-359.
Tang et al., Genetic Immunization Is a Simple Method for Eliciting an Immune Response. Nature Mar. 1992;356(6365): 152-154.

(56) References Cited

OTHER PUBLICATIONS

Timares et al., Quantitative Analysis of the Immunopotency of Genetically Transfected Dendritic Cells. PNAS Oct. 27, 1998;95(22): 13147-13152.
UniPROTKB R5P6I5_9BACT, Mar. 15, 2017 [online]. Retrieved on Jan. 24, 2020] from the Internet <URL:https://linkprotect.cudasvc.com/url?a=https%3a%2f%2fwww.uniprot.org%2funiprot%2fR5P6I6.AYCY%3fversion%3d10&c=E,1,vujsqy5TRr_U35_1YBVS1rbhVWSGyEB12uM3LhAfKr4IROEfYIVBtGvz5bc2mP7vR9wt8iNvStZXhd2PDIN4sjP6hdPbd6ZZbEJfLarPtZj5DoMeYtDzis0,&typo=0> Amino Acids 121-135, 66.3% identity to Seq ID No. 3 (2 pages).
UniPROTKB A9V5X0_MONBE, Mar. 28, 2018 [online]. Retrieved on Jan. 24, 2020 from the internet ,URL:https://linkprotect.cudascv.com/url?a=https%3a%2f%2fwww.uniprot.org%2funiprot%2fA9V5X0.txt%3fversion%3d40&c=E,1,YC45ztA63iYZyJnWnuFaCIKCemM4Eo-Fv_wh2OzFlqCMoXYkdK0UF77xKX4L8rbQO1n-X7JYz72WUvE23ETf_BkC_T7mkMT6zkmfFFuoqNFAti6ZawzDw,,&typo+0> Amino Acids 1262-1276, 67.4% identity to Seq ID No. 5 (3 pages).
UniPROTKB I1B218_9RHOB, Feb. 28, 2018 [online] retrieved on Jan. 24, 2020 from the internet <URL:https://linkprotect.cudasvc.com/url?a=https%3a%2f%2fwww.uniprot.org%2funiprot%2fI1B218.txt%3fversion%3d15%c=E, 1,zqlHjk#bxlfUnHj3nqLaZ_dpGmdYuOghUMJzIB-gxyg9cCdO40G3X0TRNn7-J-WNtYFhqW7BMHwzTxViFJAgD0JQuHgttbkXC2BrGvePf-oC8_1i9Bw,,&typo=0> Amino Acids 44-58, 67.4% identity to SeqId No. 8, (2 pages).
Untergasser et al., Primer3Plus, an Enhanced Web Interface to Primer3. Nucleic Acids Res. Jul. 1, 2007;35(suppl_2): W71-W74.
Usmani B.A., Genomic Instability and Metastatic Progression. Pathobiology 1993;61(2): 109-116.
Varga et al., Infectious Entry Pathway of Adenovirus Type 2. J Virol. Nov. 1991;65(11): 6061-6070.
Vella et al., Healthy Individuals Have T-Cell and Antibody Responses to the Tumor Antigen Cyclin B1 That When Elicited in Mice Protect from Cancer. PNAS U S A. Aug. 18, 2009;106(33): 14010-14015.
Verhoeyen et al., Reshaping Human Antibodies: Grafting an Antilysozyme Activity. Science 1988;239:1534-1536.
Vesely et al., Cancer Immunoediting: Antigens, Mechanisms, and Implications to Cancer Immunotherapy. Ann N Y Acad Sci. 2013;1284: 1-5.
Vitiello et al., Neoantigen Prediction and the Need for Validation. Nat Biotech. Sep. 2017;35(9): 815-817.
Vogelstein et al., Cancer Genome Landscapes. Science. Mar. 29, 2013;339(6127): 1546-1558.
Vonderheide et al., Immunotherapy at Large: The Road to Personalized Cancer Vaccines. Nat Med Sep. 6, 2013;19(9): 1098-1100.
Vranic S., Microsatellite Instability Status Predicts Response to Anti-PD-1/PD-L1 Therapy Regardless the Histotype: A Comment on Recent Advances. Bosn J Basic Med Sci. Aug. 2017;17(3): 274-275.
Wang et al., Utilization of an Alternative Open Reading Frame of a Normal Gene in Generating a Novel Human Cancer Antigen. J Exper Med. Mar. 1, 1996;183(3): 1131-1140.
Wang et al., Differences in Microsatellite Instability Profiles Between Endometrioid and Colorectal Cancers: A Potential Cause for False-Negative Results? J Mol Diag. Jan. 1, 2017;19(1): 57-64.
Ward et al., Binding Activities of a Repertoure of Single Immunoglobulin Variable Domains Secreted from *Escherichia coli*. Nature Oct. 12, 1989;341(6242): 544-546.
Weinschenk et al., Integrated Functional Genomics Approach for the Design of Patient-individual Antitumor Vaccines. Cancer Res. Oct. 15, 2002;62(20): 5818-5827.
Whitlock et al., Protective Antigens Against Glanders Identified by Expression Library Immunization. Front Microbiol. Nov. 21, 2011;2: 227 (14 pages).
Whittemore et al., A General Method to Discover Epitopes from Sera. PLoS One. Jun. 13, 2016;11(6): e157462, 13 pages.

Woerner et al. Systematic Identification of Genes With Coding Microsatellites Mutated in DNA Mismatch Repair-Deficient Cancer Cells. Int J Cancer, Jul. 1, 2001;93(1): 12-19.
Wolchok et al., Phase I Trial of High Dose Paracetamol and Carmustine in Patients With Metastatic Melanoma. Melanoma Res. Apr. 1, 2003;13(2): 189-196.
Wolff et al., Direct Gene Transfer Into Mouse Muscle In Vivo. Science Mar. 23, 1990;247(4949 Pt 1): 1465-1468.
Xu et al., Research Progress in Clinical Treatment of Tumor Immune Checkpoint Inhibitors. China Clinical Pharmacology and Therapeutics, Feb. 2016;21(2): 218-224.
Yannelli et al., Development of an Autologous Canine Cancer Vaccine System for Resectable Malignant Tumors in dogs. Vet Immun Immunopath. Dec. 1, 2016;182: 95-100.
Zabner, Safety and Efficacy of Repetitive Adenovirus-Mediated Transfer of CFTR cDNA to Airway Epithelia of Primates and Cotton Rats. Nat Genet. Jan. 1994;6(1): 75-83.
Zaher et al., Fidelity at the Molecular Level: Lessons from Protein Synthesis. Cell Feb. 20, 2009;136(4): 746-762.
Zhang et al., Generation and Identification of Recombinant Adenovirus by Liposome-Mediated Transfection and PCR Analysis. BioTechniques Nov. 1, 1993;15(5): 868-872.
Zhang J., Frameshift Antigens for Cancer Vaccine Development. Doctoral Thesis; Arizona State University. May 31, 2018, 234 pages.
Zhang et al., Using Frameshift Peptide Arrays for Cancer Neo-Antigens Screening. Sci Reports. Nov. 26, 2018;8(1): 10 pages.
Zöller M.J., New recombinant DNA methodology for protein engineering. Curr Opin. Biotech. Aug. 1, 1992;3(4): 348-354.
Zöller et al., Prophylactic Tumor Vaccination: Comparison of Effector Mechanisms Initiated by Protein Versus DNA Vaccination. J Immunol. Mar. 2001; 1;166(5): 3440-3450.
Zuker M., On Finding All Suboptimal Foldings of an RNA Molecule. Science Apr. 7, 1989;244(4900): 48-52.
Agarwal et al., Disregulated Expression of the Th2 Cytokine Gene in Patients With Intraoral Squamous Cell Carcinoma. Immunol Invest. Jan. 1, 2003;32(1-2): 17-30.
Altschul et al., Basic Local Alignment Search Tool. J. Mol. Biol. Oct. 5, 1990;215(3): 403-410.
Altschul et al., Issues in Searching Molecular Sequence Databases. Nature Genet. Feb. 1994;6(2): 119-129.
Anderson et al., The Human Plasma Proteome: History, Character, and Diagnostic Prospects. Mol Cell Proteo. Nov. 1, 2002;1(11): 845-867; and Additions & Corrections (1 page).
Andresen et al., Deciphering the Antibodyome—Peptide Arrays for Serum Antibody Biomarker Diagnostics. Curr Proteo. Apr. 1, 2009;6(1): 1-12.
Anonymous, NSB9; NSB Postech, Inc., 2007, in 4 pages.
Anonymous, Affymetrix; GeneChip Human Genome Arrays Data Sheet, 2003, in 4 pages.
Bailey, Meme: Discovering and analyzing DNA and Protein Sequence Motifs. Nucl Acids Res. Jul. 1, 2006;34(suppl_2): W369-W373.
Bartolomé et al., Activated Gα13 Impairs Cell Invasiveness Through p190RhoGAP-mediated Inhibition of RhoA Activity. Cancer Res. Oct. 15, 2008;68(20): 8221-8230.
Bauer et al., Identification and Quantification of a New Family of Peptide Endocannabinoids (Pepcans) Showing Negative Allosteric Modulation at CB1 Receptors. J Biol Chem. Oct. 26, 2012;287(44): 36944-36967.
Berglund et al., A Genecentric Human Protein Atlas for Express Profiles Based on Antibodies. Mol Cell Proteo. Oct. 1, 2008;7(10): 2019-2027.
Betanzos et al., Bacterial Glycoprofiling by Using Random Sequence Peptide Microarrays. ChemBioChem. Mar. 23, 2009;10(5): 877-888.
Bitter et al., Expression and Secretion Vectors for Yeast. Methods Enzymol. 1987;153: 516-544.
Boltz et al., Peptide Microarrays for Carbohydrate Recognition. Analyst. 2009;134(4): 650-652.
Borrebaeck C.A.K., Antibodies in Diagnostics—From Immunoassays to Protein Chips. Immun Today. Aug. 1, 2000;21(8): 379-382.
Breitling, High-Density Peptide Arrays. Mol BioSys. 2009;5(3): 224-234.

(56) References Cited

OTHER PUBLICATIONS

Brown et al., The Preclinical Natural History of Serous Ovarian Cancer: Defining the Target for Early Detection. PLoS Med. Jul. 2009;6(7): e1000114; 14 pages.
Brown et al., Statistical Methods for Analyzing Immunosignatures. BMC Bioinfo. Dec. 2011;12(1): 1-5.
Brusic et al., Information Technologies for Vaccine Research. Expert Rev Vaccines. Jun. 2005;4(3): 407-417.
Butler et al., The Immunochemistry of Sandwich ELISAs—VI. Greater Than 90% of Monoclonal and 75% of Polyclonal Anti-Fluorescyl Capture Antibodies (CAbs) are Denatured by Passive Adsorption. Mol Immunol. Sep. 1, 1993;30(13): 1165-1175.
Butler J.E., Solid Supports in Enzyme-Linked Immunosorbent Assay and Other Solid-Phase Immunoassays. Methods. Sep. 2000;22(1): 4-23.
Casey et al., Phage Display of Peptides in Ligand Selection for Use in Affinity Chromatography. Methods Mol Biol. 2008;421: 111-124.
Cenci et al., Managing and Exploiting Stress in the Antibody Factory. FEBS Lttrs. Jul. 31, 2007;581(19): 3652-3657.
Cerecedo et al., Mapping of the IgE and IgG4 Sequential Epitopes of Milk Allergens with a Peptide Microarray-Based Immunoassay. J All Clin Immunol. Sep. 1, 2008;122(3): 589-594.
Chase et al., Evaluation of Biological Sample Preparation for Immunosignature-Based Diagnostics. Clin Vac Immunol. Mar. 2012;19(3): 352-358.
Chen et al., Identification of Multiple Cancer/Testis Antigens by Allogeneic Antibody Screening of a Melanoma Cell Line Library. PNAS Jun. 9, 1998;95(12): 6919-6923.
Chen et al., Autoantibody Profiles Reveal Ubiquilin 1 as a Humoral Immune Response Target in Lung Adenocarcinoma. Cancer Res. Apr. 1, 2007;67(7): 3461-3467.
Chène P., Challenges in Design of Biochemical Assays for the Identification of Small Molecules to Target Multiple Conformations of Prein Kinases. Drug Discover Today. Jun. 1, 2008;13(11-12): 522-529.
Christian et al., Simplified Methods for Construction, Assessment and Rapid Screening of Peptide Libraries in Bacteriophage. J Mol Biol. Oct. 5, 1992;227(3): 711-718.
Cooperman et al., Cell Division Rates of Primary Human Precursor B Cells in Culture Reflect in vivo Rates. Stem cells. Nov. 2004;22(6): 1111-1120.
Corpet F., Multiple Sequence Alignment with Hierarchical Clustering. Nucl Acids Res. Nov. 25, 1988;16(22): 10881-10890.
Cotter et al., Molecular Genetic Analysis of Herpesviruses and Their Potential Use as Vectors for Gene Therapy Applications. Curr Opin Mol Thera. Oct. 1, 1999;1(5): 633-644.
Cretich, Protein and Peptide Arrays: Recent Trends and New Directions. Biomol Eng. Jun. 1, 2006;23(2-3): 77-88.
Cretich et al., Epitope Mapping of Human Chromogranin A by Peptide Microarrays. Chapter 10; Pept Micro. Jan. 1, 2009;570: 221-232.
Daver et al., The Usefulness of Prostate-Specific Antigen and Prostatic Acid Phosphatase in Clinical Practice. Am J Clin Oncol. Jan. 1988; 11 (Suppl 2): S53-S60.
DeNiro et al., Zinc Transporter 8 (ZnT8) Expression is Reduced by Ischemic Insults: A Potential Therapeutic Target to Prevent Ischemic Retinopathy. PLoS One. Nov. 27, 2012;7(11): e50360.
Derda et al., Diversity of Phage-Displayed Libraries of Peptides During Panning and Amplification. Mol. Feb. 21, 2011;16(2): 1776-1803.
De Vegvar et al., Microarray Profiling of Antiviral Antibodies for the Development of Diagnostics, Vaccines, and Therapeutics. Clin Immunol. May 1, 2004;111(2): 196-201.
Diehnelt et al., Discovery of High-Affinity Protein Binding Ligands-Backwards. PLoS One. May 19, 2010;5(5): e10728.
Draghici S., Statistics and Data Analysis for Microarrays Using R and Bioconductor. Chapman & Hall/CRC Press. 2nd Edition; Apr. 18, 2016; TOC in 33 pages.

Engvall et al., Enzyme-Linked Immunosorbent Assay (ELISA). Quantitative Assay of Immunoglobulin G. Immunochem. Sep. 1971;8(9): 871-874.
Falsey et al., Peptide and Small Molecule Microarray for High Throughput Cell Adhesion and Functional Assays. Bioconj Chem. May 16, 2001;12(3): 346-353.
Fodor et al., Multiplexed Biochemical Assays with Biological Chips. Nature. Aug. 5, 1993;364(6437): 555-556.
Folgori et al., A General Strategy to Identify Mimotopes of Pathological Antigens Using Only Random Peptide Libraries and Human Sera. EMBO J. May 1994;13(9): 2236-2243.
Foong et al., Current Advances in Peptide and Small Molecule Microarray Technologies. Curr Opin Chem Biol. Apr. 1, 2012;16(1-2): 234-242.
Förster et al., The Bulk of the Peripheral B-Cell Pool in Mice is Stable and not Rapidly Renewed from the Bone Marrow. PNAS Jun. 1990;87(12): 4781-4784.
Frith. Discovering Sequence Motifs with Arbitrary Insertions and Deletions. PLoS Comp Biol. May 9, 2008:4(5): e1000071.
Fu et al., Exploring Peptide Space for Enzyme Modulators. J Am Chem Soc. May 12, 2010;132(18): 6419-6424.
Fu et al., Peptide-Modified Surfaces for Enzyme Immobilization. PLoS One Apr. 8, 2011;6(4): e18692.
Gallina et al., Prediction of Pathological Stage is Inaccurate in Men with BSA Values above 20 ng/mL. Eur Urol. Nov. 2007;52(5): 1374-1380. Epub Dec. 11, 2006.
Geysen et al., Use of Peptide Synthesis to Prove Viral Antigens for Epitopes to a Resolution of a Single Amino Acid. PNAS Jul. 1984;81(13): 3998-4002.
Greving et al., Thermodynamic Additivity of Sequence Variations: An Algorithm for Creating High Affinity Peptides without Large Libraries or Structural Information. PLoS One. Nov. 2010;5(11): e15432.
Greving et al., High-Throughput Screening in Two Dimensions: Binding Intesity and Off-rate on a Peptide Microarray. Anal Biochem. Jul. 1, 2010;402(1): 93-95.
Gupta et al., Engineering a Synthetic Ligand for Tumor Necrosis Factor-α. Bioconj Chem. Aug. 17, 2011;22(8): 1473-1478; Epub Nov. 9, 2010.
Halperin R., Characterization and Analysis of a Novel Platform for Profiling the Antibody Response. Doctoral Dissertation, Arizona State University 2011, in 272 pages.
Halperin et al., GuiTope: An Application for Mapping Random-Sequence Peptides to protein Sequences. BMC Bioinfo. Dec. 2012;13(1): 1-8.
Hampe C.S., B Cells in Autoimmune Diseases. Scientifica Oct. 2012; Article ID 215308, in 18 pages.
Hanash S., Disease Proteomics. Nature Mar. 2003;422(6928): 226-232.
Hao et al., Homeostasis of Peripheral B Cells in the Absence of B Cell Influx from the Bone Marrow. J Exp Med. Oct. 15, 2001;194(8): 1151-1164.
Hecker et al., Computational Analysis of High-density Peptide Microarray Data with Application from Systemic Sclerosis to Multiple Sclerosis. Autoimmun Rev. Jan. 1, 2012;11(3): 180-190.
Higgins et al., CLUSTAL: A Package for Performing Multiple Sequence Alignment on a Microcomputer. Gene. Dec. 15, 1988;73(1): 237-244.
Higgins et al., Fast and Sensitive Multiple Sequence Alignments on a Microcomputer. Comput Appl Biosci. Apr. 1989;5(2): 151-153.
Hilpert et al., Cellulose-bound Peptide Arrays: Preparation and Applications. Biotech Gen Engin Rev. Jan. 1, 2007;24(1): 31-106.
Hori et al., Mathematical Model Identifies Blood Biomarker-Based Early Cancer Detection Strategies and Limitations. Sci Transl Med. Nov. 16, 2011;3(109): 109-116.
Huang et al., MIMOX: A Web Tool for Phage Display Based Epitope Mapping. BMC Bioinformatics. Oct. 12, 2006;7: 451 in 10 pages.
Hughes et al., Immunosignaturing Can Detect Products from Molecular Markers in Brain Cancer. PLoS One. Jul. 16, 2012;7(7): e40201.
Jagger et al., An Overlapping Protein-Coding Region in Influenza A Virus Segment 3 Modulates the Host Response. Science. Jul. 13, 2012;337(6091): 199-204.

(56) References Cited

OTHER PUBLICATIONS

Jonassen I., Efficient Discovery of Conserved Patterns Using a Pattern Graph. Comp Appl Biosci. Oct. 1, 1997;13(5): 509-522.
Kroening et al., Autoreactive Antibodies Rased by Self-derived de novo Peptides Can Identify Unrelated Antigens on Protein Microarrays. Are Autoantibodies Really Autoantibodies? Exp Mol Pathol. Jun. 1, 2012;92(3): 304-311.
Kukreja et al., Immunosignaturing Microarrays Distinguish Antibody Profiles of Related Pancreatic Diseases. J Proteo Bioinfo. 2012;S6(001): 5 pages.
Kukreja et al., Comparative Study of Classification Algorithms for Immunosignaturing Data. BMC Bioinfo. Dec. 2012;13(1): 1-25.
Lewczuk et al., Amyloid β Peptides in Plasma in Early Diagnosis of Alzheimer's Disease: A Multicenter Study with Multiplexing. Exp Neurol. Jun. 1, 2010;223(2): 366-370.
Lin et al., Development of a Novel Peptide Microarray for Large-Scale Epitope Mapping of Food Allergens. J Allergy Clin Immunol. Aug. 1, 2009;124(2): 315-322.
Liu et al., Towards Proteome-Wide Production of Monoclonal Antibody by Phage Display. J Mol Biol. Feb. 1, 2002;315(5): 1063-1073.
Liu et al., Combinatorial Peptide Library Methods for Immunobiology Research. Exp Hematol. Jan. 1, 2003;31(1): 11-30.
Lorenz et al., Probing the Epitope Signatures of igG Antibodies in Human Serum from Patients with Autoimmune disease. Chapter 18; Meth Mol Biol. 2009;524: 247-258.
Mackey et al., Getting More From Less: Algorithms for Rapid Protein Identification with Multiple Short Peptide Sequences. Mol Cell Proteo. Feb. 1, 2002;1(2): 139-147.
Marks et al., By-passing immunization. Human antibodies from V-gene libraries displayed on phage. J Mol Biol. Dec. 5, 1991;222(3): 581-597.
Matsui et al., Hepatitis C Virus Infection Suppresses GLUT2 Gene Expression via Downregulation of Hepatocyte Nuclear Factor 1α. J Virol. Dec. 1, 2012;86(23): 12903-12911.
McDade et al., What a Drop Can Do: Dried Blood Spots as a Minimally Invasive Method for Integrating Biomarkers Into Population-Based Research. Demography, 2007;44(4): 899-925.
Merbl et al., A Systems Immunology Approach to the Host-Tumor Interation: Large-Scale Patterns of Natural Autoantibodies Distinguish Healthy and Tumor-Bearing Mice. Plos One. Jun. 25, 2009;4(6): e6053.
Merriam-Webster Dictionary, "Putative" Definition 2020, 1-2; online from https://www.merriam-webster.com/dictionary/putative#learnmore on Mar. 24, 2020.
Merriam-Webster Dictionary, "Putative" Definition 2020, 1-5; online from https://www.merriam-webster.com/dictionary/putative on Jan. 2, 2020.
Mestas et al., Of Mice and Not Men: Differences Between Mouse and Human Immunology. J Immunol. Mar. 1, 2004;172(5): 2731-2738.
Miller et al., Basic Concepts of Microarrays and Potential Applications in Clinical Microbiology. Clin Microbiol Rev. Oct. 2009;22(4): 611-633.
Min et al., Peptide Arrays: Towards Routine Implementation. Curr Opin Chem Biol. Oct. 1, 2004;8(5): 554-558.
Miseta et al., Relationship Between the Occurrence of Cysteine in Proteins and the Complexity of Organisms. Mol Biol Evol. Aug. 1, 2000;17(8): 1232-1239.
Mohan et al., Association Energetics of Cross-Reactive and Specific Antibodies. Biochem. Feb. 17, 2009;48(6): 1390-1398.
Möller et al., DNA Probes on Chip Surfaces Studied by Scanning Force Microscopy Using Specific Binding of Colloidal Gold. Nucleic Acids Res. Oct. 15, 2000:28(20): e91 in 5 pages.
Moreau et al., Discontinuous Epitope Prediction Based on Mimotope Analysis. Bioinform. May 1, 2006;22(9): 1088-1095; Epub Jan. 24, 2006.
Navalkar et al., Peptide Based Diagnostics: Are Random-Sequence Peptides More Useful Than Tiling Proteome Sequences? J Immunol Meth. Feb. 1, 2015;417: 10-21.
Nobrega et al., Functional Diversity and Clonal Frequencies of Reactivity in the Available Antibody Repertoire. Eu J Immunol 1998Apr;28(4): 1204-1215.
Oltean et al., Hallmarks of Alternative Splicing in Cancer. Oncogene Nov. 2014;33(46): 5311-5318.
Panicker et al., Recent Advances in Peptide-Based Microarray Technologies. Comb Chem High Throughput Screen. Sep. 1, 2004;7(6): 547-556.
Perez-Gordo et al., Epitope Mapping of Atlantic Salmon Major Allergen by Peptide Microarray Immunoassay. Int Arch Allergy Immunol. 2012; 157(1): 31-40.
Price et al., On Silico Peptide Microarrays for High-Resolution Mapping of Antibody Epitopes and Diverse Protein-Protein Interactions. Nat Med. Sep. 2012;18(9): 1434-1440.
Quackenbush J., Computational Analysis of Microarray Data. Nature Rev. Jun. 2001;2(6): 418-427.
Quintana et al., Antigen-Chip Technology for Accessing Global Information About the State of the Body. Lupus Jul. 2006; 15(7): 428-430.
Quintana et al., The Natural Autoantibody Repertoire and Autoimmune Disease. Biomed Pharmaco. Jun. 1, 2004;58(5): 276-281.
Reddy et al., Protein "Fingerprinting" in Complex Mixtures With Peptoid Microarrays. PNAS Sep. 6, 2005;102(36): 12672-12677.
Reddy et al., Identification of Candidate IgG Biomarkers for Alzheimer's Disease via Combinatorial Library Screening. Cell Jan. 7, 2011;144(1): 132-142.
Reineke et al., Identification of Distinct Antibody Epitopes and Mimotopes From a Peptide Array of 5520 Randomly Generated Sequences. J Immunol Meth. Sep. 1, 2002;267(1): 37-51.
Reineke et al., Epitope Mapping Protocols. Meth Mol Biol. 524, 2nd Edition, Humana Press. 2009; 1-447.
Restrepo et al., Application of Immunosignatures to the Assessment of Alzheimer's Disease. Annlas Neurol. Aug. 2011;70(2): 286-295.
Rigoutsos. Combinatorial Pattern Discovery in Biological Sequences: The TEIRESIAS Algorithm. BioInform. (Oxford, England) Jan. 1, 1989;14(1): 55-67.
Rigoutsos. In Silico Pattern-Based Analysis of the Human Cytomegalovirus Genome. J Virol. Apr. 1, 2003;77(7): 4326-4344.
Roobol M.J., Contemporary Role of Prostate Cancer Gene 3 in the Management of Prostate Cancer. Curr Opin Urol. May 1, 2011;21(3): 225-229.
Schnölzer et al., Constructing Proteins by Dovetailing Unprotected Synthetic Peptides: Backbone-Engineered HIV Protease. Science. Apr. 10, 1992;256(5054): 221-225.
Shreffler et al., IgE and IgG4 Epitope Mapping by Microarray Immunoassay Reveals the Diversity of Immune Response to the Peanut Allergen. Ara h2. J All Clin Immunol. Oct. 1, 2005;116(4): 893-899.
Silverman G., Regulatory Natural Antibodies to Apoptotic Cells: Pallbearers and Protectors. Arth Rheum. Mar. 2011;63(3): 597-602.
Sulzer et al., Memory in Idiotypic Networks Due to Competition Between Proliferation and Differentiation. Bull Math Biol. Nov. 1, 1993;55(6): 1133-1182.
Szardenings M., Phage Display of Random Peptide Libraries: Applicationis, Limits, and Potential. J Recept Sig Transd. Jan. 1, 2003;23(4): 307-349.
Tang et al., Current Developments in SELDI Affinity Technology. Mass Spectrom. Rev. 2004;23: 34-44.
Tedesco et al., A New Strategy for the Early Diagnosis of Rheumatoid Arthritis: A Combined Approach. Autoimmun Review. Jan. 1, 2009;8(3): 233-237.
Thompson et al., Prostate-Specific Antigen in the Early Detection of Prostate Cancer. CMAJ Jun. 19, 2007;176(13): 1853-1858.
Thorpe et al., Molecular Evolution of Affinity and Flexibility in the Immune System. PNAS May 22, 2007 May; 104(21): 8821-8826.
Uhlén et al., Generation and Validation of Affinity Reagents on a Proteome-Wide Level. J Mol Recogn. Mar. 2009;22(2): 57-64.
Usami et al., The Effect of pH, Hydrogen Peroxide and Temperature on the Stability of Human Monoclonal Antibody. J Pharm Biomed Anal. Jun. 1996;14(8-10): 1133-1140.
Volk et al., The Accuracy of Primary Care Patients' Self-Reports of Prostate-Specific Antigen Testing. Am J Prev med. Jan. 2002;22(1): 56-58.

(56) References Cited

OTHER PUBLICATIONS

Wang et al., Detection of Mammary Tumor Virus ENV Gene-Like Sequences in Human Breast Cancer. Nov. 15, 1995;55(22): 5173-5179.

Waterboer et al., Dried Blood Spot Samples for Seroepidemiology of Infections With Human Papillomaviruses. Cancer Epidem Biomarkers Prevent. Feb. 1, 2012;21(2): 287-293.

Yang et al., Segmentation and Intensity Estimation for Microarray Images With Saturated Pixels. BMC Bioinfo. Dec. 2011;12(1): 462, 11 pages.

Zhou et al., Properties and Function of Polyreactive Antibodies and Polyreactive Antigen-Binding B Cells. Autoimmun. Dec. 1, 2007;29(4): 219-228.

Zundel et al., Development and Evaluation of an Enzyme-Linked Immunoassay for the Prostate: Specific Antigen Utilizing Two Monoclonal Antibodies. Urol Res. 1990;18(5): 327-330.

\* cited by examiner

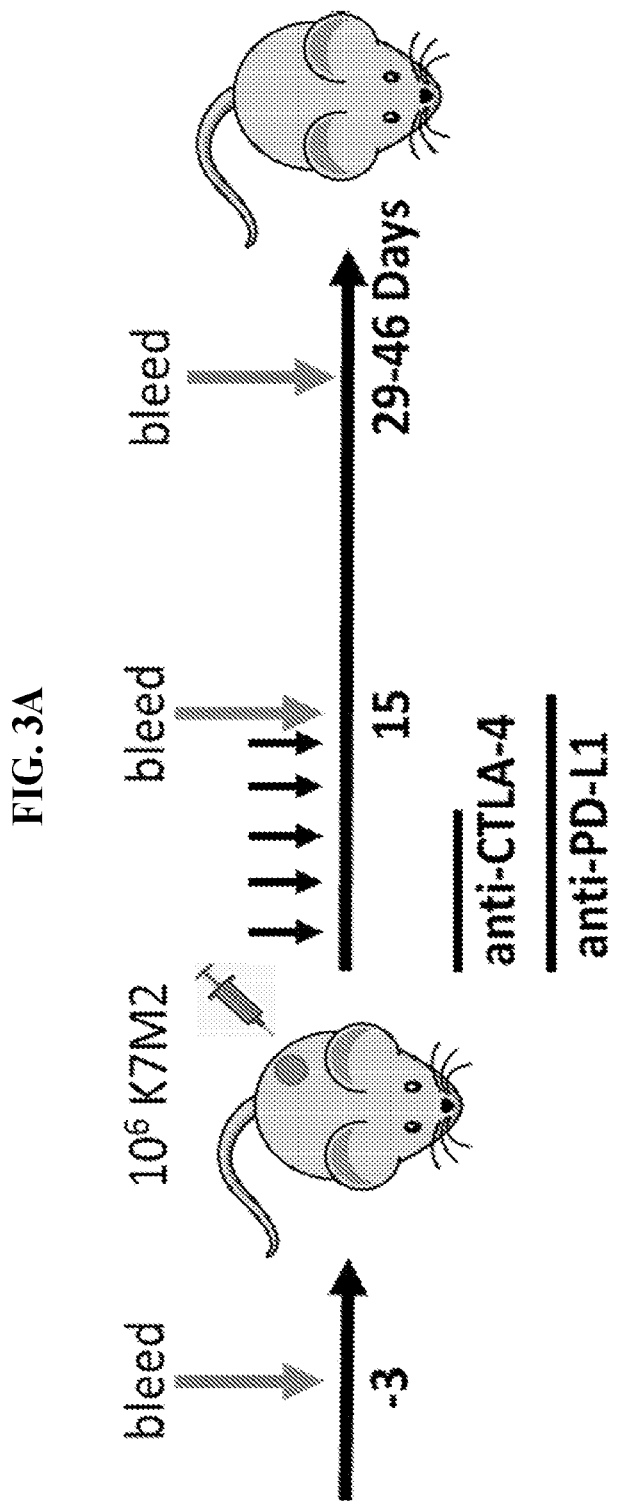

33 FS Array Peptides

FIG. 12A-12B, CONTINUED
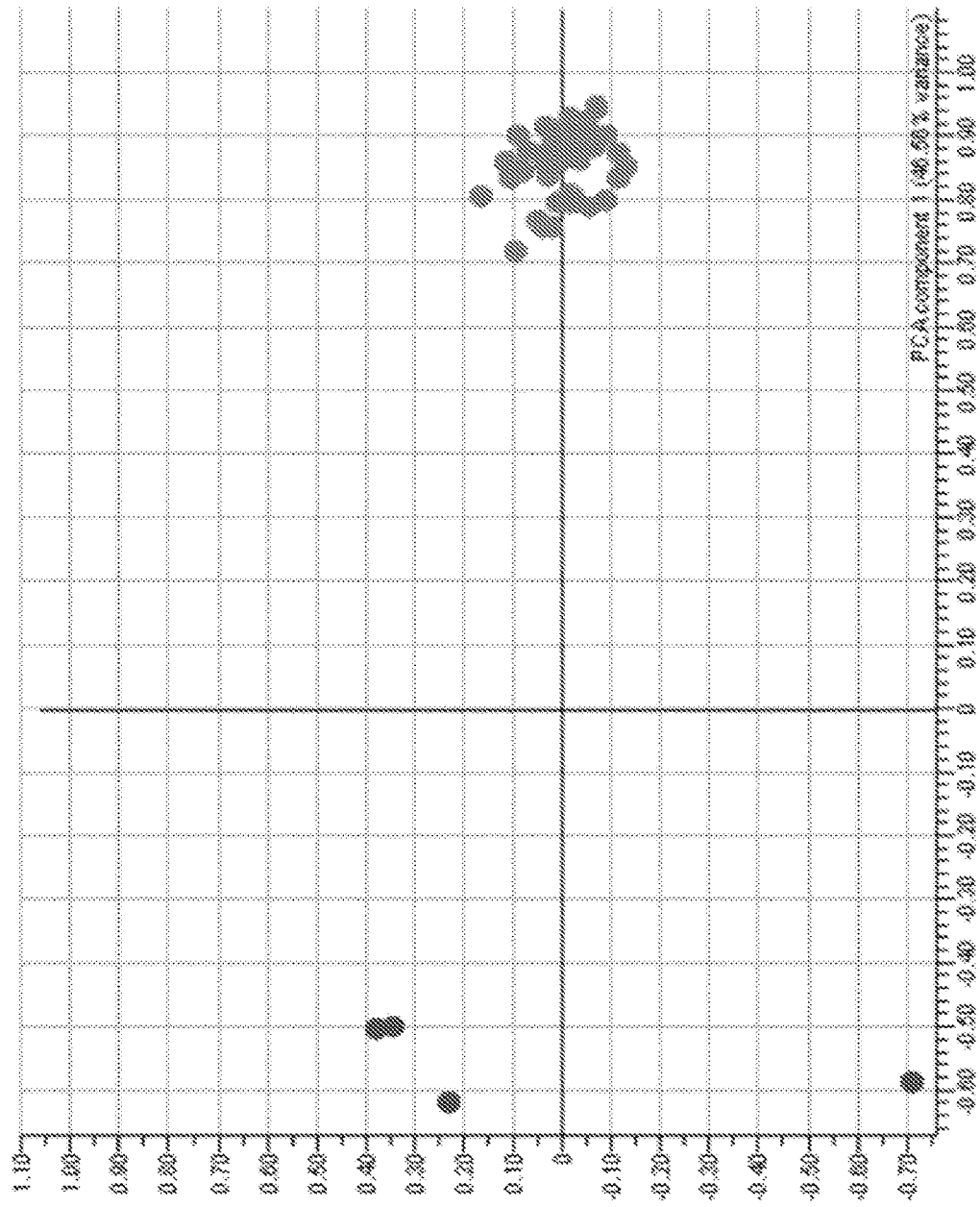
B.

METHODS OF CLASSIFYING RESPONSE TO IMMUNOTHERAPY FOR CANCER

CROSS-REFERENCE TO RELATED APPLICATIONS

This application is a divisional of U.S. application Ser. No. 16/647,434, filed Mar. 13, 2020, which is a U.S. national phase application of PCT international application No. PCT/US2018/050827 filed Sep. 13, 2018, which claims the benefit of U.S. Provisional Patent Application No. 62/559,337, filed Sep. 15, 2017; this application claims the benefit of each of the foregoing and each is incorporated herein by reference as if set forth in its entirety.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

STATEMENT REGARDING FEDERALLY SPONSORED R&D

Not applicable.

BACKGROUND OF THE INVENTION

Field of the Invention

This application relates to methods and compositions that allow the prediction of a response of a patient to therapeutic treatment with immunomodulators such as checkpoint inhibitors. The prediction could be relative to the therapeutic response or side-effects. The application also bears on prognosis in general for cancer outcomes.

Description of the Related Art

The treatment of cancer has been transformed over the last few years by the development of immunotherapeutics (IT). Immunotherapeutics include checkpoint inhibitors which enhance the natural anti-tumor immune response or help augment personal, neoepitope vaccines. Immunotherapeutics also include cell-based therapies such as adoptive T-cell therapies in which large numbers of a patient's T-cells are modified ex vivo to express chimeric antigen receptors (CARs) and returned to the patient as engineered T-cells.

However, this revolution has limitations. Immunotherapeutic treatments are very expensive, in some cases between $150,000 and $450,000 or more. On average only about 25% of patients who receive immunotherapy have a positive clinical response to the treatment. In addition, there can be severe side-effects, including death.

This has spurred an effort to identify biomarkers that could distinguish patients more likely to have a positive response and to predict which patients would have deleterious side effects. Initially the level of expression of PDL-1 on the tumor cells was used as a correlate of protection. This is currently being used as a biomarker in spite of its low predictive value. As the DNA sequences of more patient tumors were analyzed, it was realized that a more relevant correlate was the level of neoantigen mutations in the DNA of the tumor. This makes sense in that the neoantigens drive the anti-tumor immune response. In special cases of microsatellite instability (MSI) the mutations in the tumor that create frameshift neoantigens are strong predictors of a positive response to therapy. The correlation was so strong that for the first time the FDA awarded Merck (now also BMS) a blanket approval to treat any cancer with MSI with anti-PD-1 antibody. However, MSI is only prevalent in a small percentages of cancer. For most cancers, the hope is that Total Mutation Burden (TMB) will be the biomarker of choice for deciding who might respond to therapy. In this protocol a portion of the DNA from a tumor biopsy is sequenced and the total number of mutations tabulated. This number is used to predict response. Though it has had marginal predictive value, it currently is the best alternative. Because of the cost and that only some tumors yield enough good DNA for sequencing, there is interest in sequencing the tumor free DNA in the blood. This carries with it other problems, notably the blood dilution issue.

A basic problem with TMB and related DNA-based approaches is that what is recorded (mutations) is far removed from the relevant biological activity—namely the immune response elicited by a neoantigen. A checkpoint inhibitor is presumed to work by blocking the down-regulatory signals on T-cells, allowing the immune response that the tumor has already elicited to be more effective. TMB measures any mutation which is indirectly related to neoantigen creating mutations. Only about 1% non-synonymous mutations are potentially immunogenic. To be immunogenic on the tumor they have to be expressed at the RNA level, be processed by the proteasome and end up on an MHC molecule—all of which steps have a finite probability of success. Given this complexity of relationships it does not seem surprising that TNIB is only weakly predictive of a positive response to checkpoint treatment. Accordingly, there is a pressing need for biomarkers that are more closely related to the biologically relevant response for screening to predict response to immunotherapeutics.

SUMMARY OF THE INVENTION

This disclosure relates to the application of methods and compositions for classification and characterization of subjects with respect to their likely response to treatment with an immunotherapeutic. In particular, this disclosure relates to the application of two peptide array formats—immunosignature (IMS) and frameshift signature (FS)—to the classification and characterization of subjects with respect to their likely response to treatment with a checkpoint inhibitors or other immunotherapeutics (IT).

In a first aspect, provided in this disclosure is a method of classifying how a subject having cancer may respond to treatment with an immunotherapeutic, the method comprising: (a) contacting a biological sample from the subject to a frameshift peptide array comprising a plurality of tumor-associated frameshift peptides; (b) detecting the presence or absence of antibodies having affinity to one or more of the frameshift peptides in the contacted biological sample; (c) quantifying a level of the antibodies having affinity to one or more of the frameshift peptides to form a frameshift signature of the subject; and (d) comparing the frameshift signature of the subject to one or more frameshift signature standards comprising a frameshift signature of one or more subjects known to respond to an immunotherapeutic treatment, and wherein the subject is classified as being likely to respond to treatment with the immunotherapeutic based on the comparison. The immunotherapeutic can be selected from the group consisting of a CTLA-4 inhibitor, a PD-L1 inhibitor, and a PD-1 inhibitor. The comparison can be predictive of the clinical outcome of the immunotherapeutic treatment in the subject. The biological sample can be a blood or tissue sample. The blood sample can be a peripheral blood sample. The cancer can be selected from the group consisting of breast cancer, renal cell carcinoma, lung cancer, and melanoma. The subject can be a mammal. The mammal can be a human. The mammal can be a canine. In some cases, the method further comprises creating a record indicating the subject is likely to respond to the immunotherapeutic treatment based on the frameshift signature. The record can be created on a computer readable medium.

In a further aspect, provided herein is a method for classifying a subject having a cancer as having a good prognosis or a poor prognosis, the method comprising the steps of: (a) contacting a biological sample from the subject to a frameshift array comprising a plurality of tumor-associated frameshift peptides; (b) detecting the presence or absence of antibodies having affinity to one or more of the frameshift peptides in the contacted biological sample; (c) quantifying a level of the antibodies having affinity to one or more of the frameshift peptides to form a frameshift signature of the subject; and (d) classifying the subject as having a good prognosis or a poor prognosis based on comparison of the subject's frameshift signature to one or more frameshift signature standards comprising a frameshift signature of one or more subjects known to respond to an immunotherapeutic treatment, wherein the good prognosis indicates that said subject is expected to have a favorable response to an immunotherapeutic treatment, and wherein the poor prognosis indicates that said subject is expected to have an unfavorable response to an immunotherapeutic treatment. The immunotherapeutic can be selected from the group consisting of a CTLA-4 inhibitor, a PD-L1 inhibitor, and a PD-1 inhibitor. The comparison can be predictive of the clinical outcome of the immunotherapeutic treatment in the subject. The biological sample can be a blood or tissue sample. The blood sample can be a peripheral blood sample. The cancer can be selected from the group consisting of breast cancer, renal cell carcinoma, lung cancer, and melanoma. The subject can be a mammal. The mammal can be a human. The mammal can be a canine. In some cases, the method further comprises creating a record indicating the subject is likely to respond to the immunotherapeutic treatment based on the frameshift signature. The record can be created on a computer readable medium.

In a further aspect, provided herein is a method of classifying whether a subject might experience an immune-related adverse event in response to treatment, the method comprising the steps of: (a) contacting a biological sample from the subject to a frameshift array comprising a plurality of tumor-associated frameshift peptides; (b) detecting the presence or absence of antibodies having affinity to one or more of the frameshift peptides in the contacted biological sample; (c) quantifying a level of the antibodies having affinity to one or more of the frameshift peptides to form a frame shift signature of the subject; and (d) classifying the subject as having a high likelihood of experiencing an adverse event based on comparison of the subject's frameshift binding pattern to one or more standards, wherein the signature distinguishes a person likely to have an adverse event from those that are unlikely to have an adverse event in response to immunotherapy. The immunotherapeutic can be selected from the group consisting of a CTLA-4 inhibitor, a PD-L1 inhibitor, and a PD-1 inhibitor. The biological sample can be a blood or tissue sample. The blood sample can be a peripheral blood sample. The subject can be a mammal. The mammal can be a human. The mammal can be a canine. The method can further comprise creating a record indicating the subject is likely to experience an adverse event in response to the immunotherapeutic treatment based on the frameshift signature. The record can be created on a computer readable medium.

In another aspect, provided in this disclosure is a method of classifying a subject having cancer as likely to respond to an IT treatment. As described herein, the method can comprise or consist essentially of: (a) contacting a biological sample from the subject to a plurality of peptides capable of off-target binding to at least one antibody in the biological sample; and (b) comparing an immunosignature of the subject to one or more immunosignature standards, wherein the subject is classified as being likely to respond to IT treatment based on the comparison. The one or more immunosignature standards can comprise at least one immunosignature of a subject or subjects known to respond to IT treatment. In some cases, the comparison is predictive of the clinical outcome of the treatment in the subject. The method can further comprise quantifying the off-target binding of the at least one antibody of the sample to one or more peptides of the plurality to form the immunosignature. The plurality of peptides can be a random peptide array. The biological sample can be a blood, tissue, or other bodily sample. The blood sample can be a peripheral blood sample. The immunotherapeutic can be selected from the group consisting of a CTLA-4 inhibitor, a PD-L1 inhibitor, and a PD-1 inhibitor. The cancer can be selected from the group consisting of renal cell carcinoma, lung cancer, and melanoma. The cancer can be a recurrent cancer. The subject can be a mammal. The mammal can be a human. The mammal can be a canine.

In some cases, the method further comprises creating a record indicating the subject is likely to respond to the checkpoint inhibitor treatment based on the immunosignature. The record can be created on a computer-readable medium.

These and other features, aspects, and advantages described herein will become better understood by persons of ordinary skill in the art upon consideration of the following drawings, detailed description, and appended claims.

BRIEF DESCRIPTION OF THE DRAWINGS

The following drawings form part of the present specification and are included to further demonstrate certain illustrative aspects of the methods provided herein, which may be better understood by reference to one or more of these drawings in combination with the detailed description of specific embodiments presented herein. Persons of ordinary skill in the art will readily recognize and appreciate that the drawings are non-limiting and presented for exemplary purposes.

FIGS. 3A-3B demonstrate that IMS can distinguish between responders to an anti-PDL1 and anti-CTLA4 combination treatment in an osteosarcoma lung metastasis mouse model. (A) After i.v. injection of K7M2 tumor cells, the mice were treated with 3 dosages of anti-PD-L1 plus anti-CTLA4 and 2 more dosages of anti-PD-L1 treatment. Each treatment was three days apart. (B) The IMS were analyzed (1) before the tumor injection and the treatment, (2) right after the treatment, and (3) at the end of the experiment when the non-respond mice died from lung metastasis. At each time point, the IMS significantly distinguished responder mice (green bar) and non-responder mice (red bar).

DETAILED DESCRIPTION OF THE PREFERRED EMBODIMENT

All publications, patents, and patent applications mentioned in this specification are herein incorporated by reference to the same extent as if each individual publication, patent, or patent application was specifically and individually indicated to be incorporated by reference.

This disclosure, by way of certain illustrative and non-limiting examples, provides methods and compositions (e.g., peptide arrays and kits) for predicting the response of a subject (such as a human or animal patient) to checkpoint inhibitor therapies. The methods and compositions provided herein are based at least in part on the appreciation that tumor mutational burden (TMB) is not reliably correlated with responsiveness to checkpoint inhibitor therapy. It was determined that the breadth and content provided by immunosignatures can be used to identify which patients are likely to respond favorably to an IT therapy and to identify subjects that are likely to be non-responsive or have adverse reactions to this form of cancer treatment.

Without being bound by any particular theory or mechanism, it is believed that the immunosignature (IMS) of a tumor better reflects the antigens being presented by the tumor to the cancer patient's immune system and that the IMS is a better correlate than mutational load for assessing responsiveness to treatment. Accordingly, IMS provides a simple and reliable method for determining with high confidence which patients are likely to respond (e.g., to respond favorably from a clinical perspective) to IT therapy. Advantageously, immunosignaturing is a more direct method of identifying subjects likely to respond to IT treatment than assessing receptor density on tumor cells or sequencing tumors to determine mutational load.

A second type of peptide array, a frameshift (FS) peptide array, is also effective in making these clinical distinctions. Unlike the IMS, FS arrays are based on the prediction of specific peptides that will be immunoreactive in cancer. It is known that tumor cells are much more prone to insert or delete nucleotides in microsatellites (thus creating indels)—both when replicating DNA and transcribing RNA—than non-cancer cells. Tumor cells are also more likely to mis-splice exons. Indels and mis-splice errors create FS peptides which are highly immunogenic. If these peptides are important in the immune response of the patient to the tumor, they are likely to be important in determining the response to IT therapy, prognosis, and the likelihood that a particular subject will experience serious side effects to IT therapy. Therefore, antibodies to these peptides are more likely to correlate with IT responses than TMB.

Methods

Figure 1:
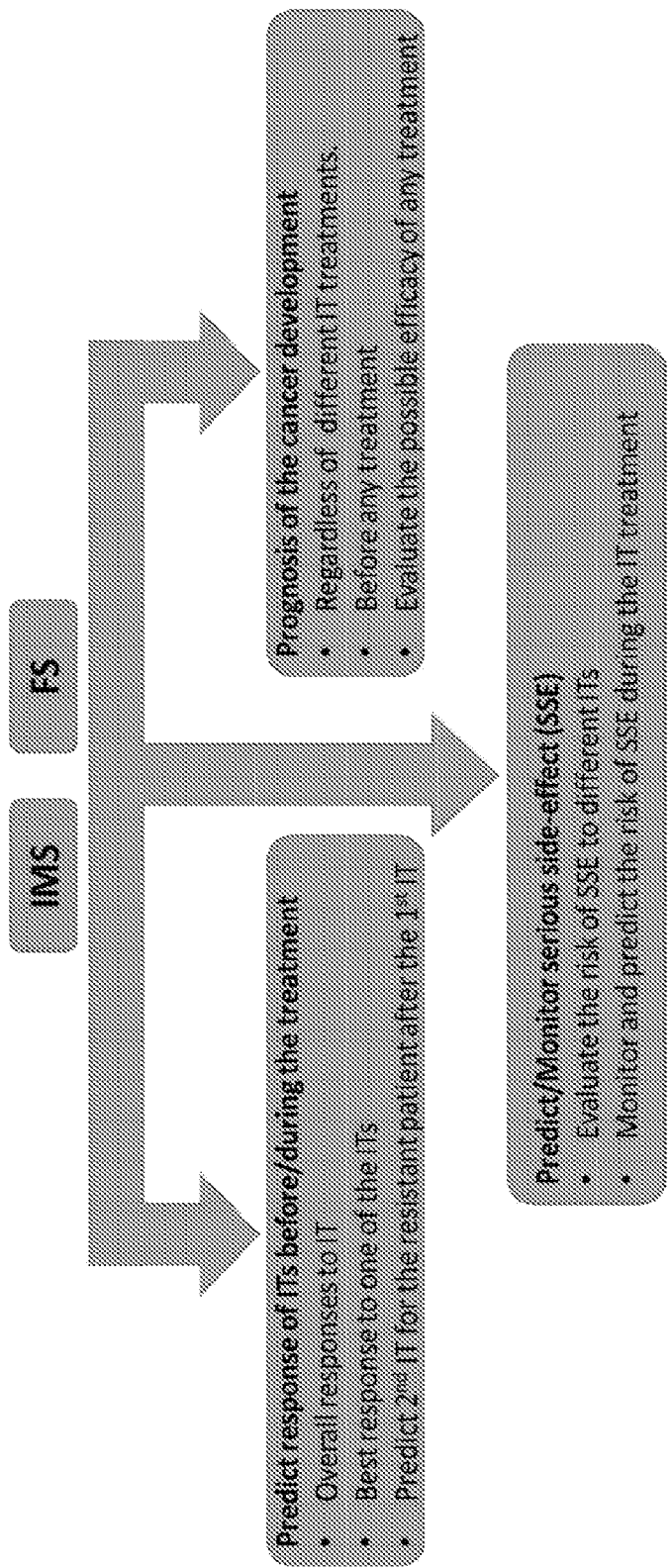
FIG. 1 is a schematic illustrating the use of immunosignatures (IMS) or frameshift signatures to (1) predict a subject's response to immunotherapeutics (IT) therapy before and during the treatment, (2) predict and monitor serious side-effects of ITs, and (3) provide a prognosis regardless of treatment. Information for these analysis can guide whether to use an IT of not and which IT to use.

Accordingly, in a first aspect, provided herein is a method of classifying how a subject having cancer is likely to respond to IT therapy and, as described herein, can include, for example, obtaining the subject's immunosignature (IMS) or Frameshift (FS) signature (or multiple immunosignatures or FS signatures) considered independently or in combination) using one or more biological samples obtained from the subject to determine whether the sample contains one or more indicators of favorable or unfavorable responses (e.g., unfavorable side effects) to IT therapy. As illustrated in FIG. 1, this disclosure also provides methods for classifying a subject as having a good prognosis or a poor prognosis for survival, and methods monitoring the effectiveness of a course of IT treatment for a subject having cancer.

The correlation between an IMS and responsiveness to IT therapy can be established by obtaining IMS profiles for subjects having a known favorable response to IT treatment and for subjects that were unresponsive or had an unfavorable response to treatment using sera (or other bodily samples) collected before each subject received treatment. In some cases, an IMS control includes non-disease sera contacted with an identical array under the same experimental conditions. The breadth of the IMS can be quantified in multiple ways including, for example the number of motifs, the percentage of signature represented, and/or total immune reactivity. Once the quantitative correlate is been established, cancer patients can be classified according to a method provided herein by quantifying a subject's signature for responsiveness to IT treatment, prognosis, or likelihood of experiencing serious side-effects of IT treatment.

Figure 2:
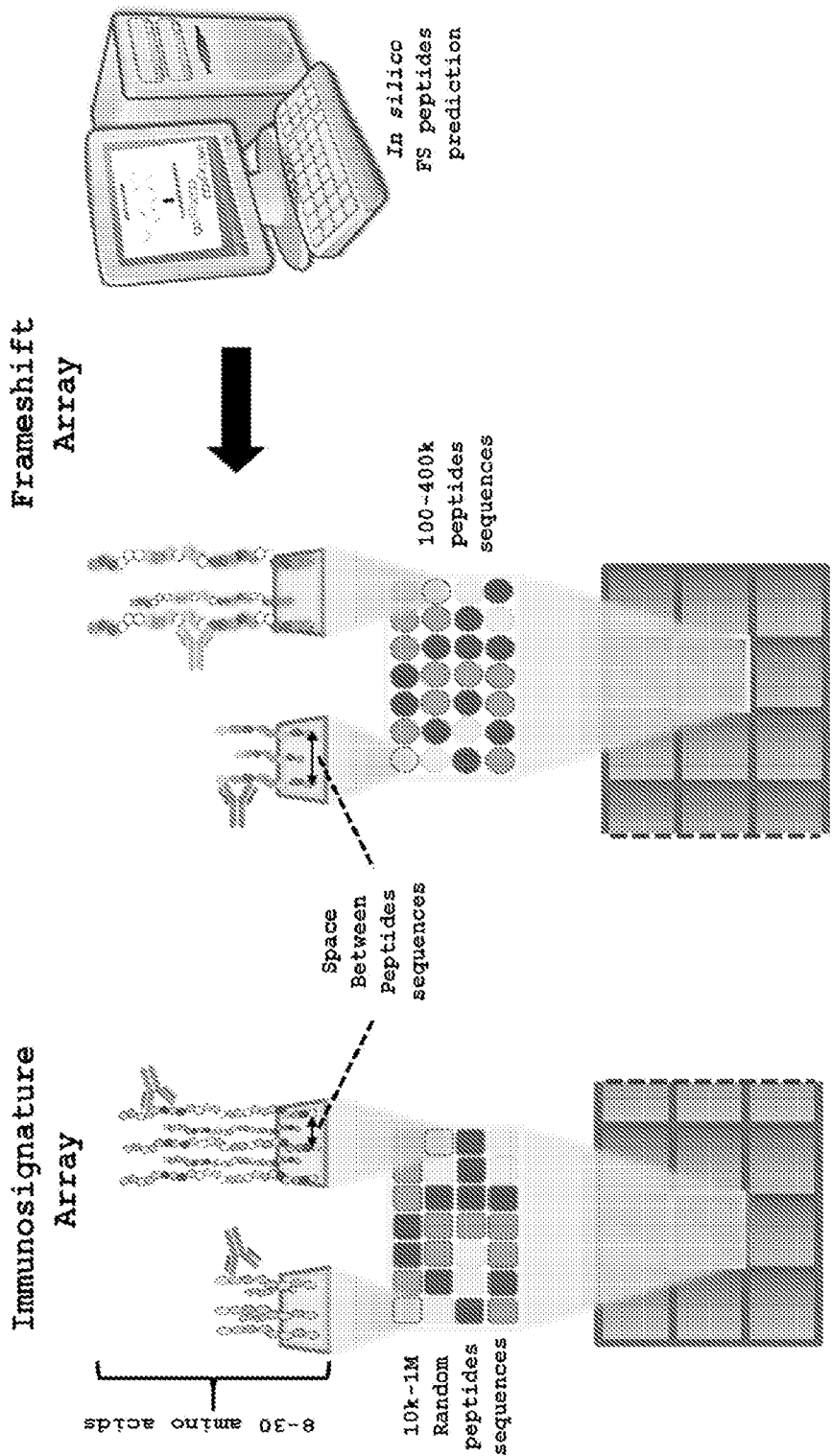
FIG. 2 illustrates two types of arrays that can be used for these distinctions: (left) Immunosignature arrays are created with about 10,000 to 1,000,000 peptides that are chosen from random sequence space. The peptides are 8-30 amino acids long are spaced to create avidity binding of antibodies for lower affinity epitopes in the peptides. (right) Frameshift arrays are created with about 100-400K peptides that are chosen from the 220,000 possible FS peptides resulting from indels in microsatellites (inserted in the DNA or only the RNA) or from mis-splicing of exons in forming the RNA. The peptides are 8-30 amino acids long and are spaced further than in IMS to enhance high affinity, cognate binding of antibodies.

Frameshift (FS) signatures provide another mechanism for classifying patients according to their responsiveness to IT treatment, prognosis, or likelihood of experiencing serious side-effects of IT treatment. In contrast to the IMS arrays, FS arrays comprise peptides selected from a finite set of approximately 220,000 possible peptides. Frameshift peptides are derived from indels in microsatellites and mis-splicing of exons. These FS peptide collections for humans and dogs have been disclosed in U.S. Patent Publication No. 2014/0087963 (filed Aug. 29, 2013), which is incorporated herein by reference as if set forth in its entirety. FS arrays can be constructed in the same manner as the IMS arrays except that, as illustrated in FIG. 2, the space between each peptide is increased to enhance cognate binding rather than mimotope binding as in IMS arrays. The sequence length of the FS peptides chosen for the array is generally 8-60 amino acids (AA) long. Peptides longer than 15 AA are represented by 2 or more peptides on the array. Accordingly, approximately 400,000 15-AA peptides on the array can represent most of the 220,000 possible FS peptides.

In certain embodiments, the methods provided herein comprise immunosignaturing (i.e., the process of detecting immunosignatures). For additional description of immunosignaturing, see U.S. Patent Publication No. 2014/0087963 (filed Aug. 29, 2013), which is incorporated herein by reference as if set forth in its entirety. Immunosignaturing displays a circulating antibody repertoire upon an addressable, machine-readable peptide microarray (e.g., a random peptide microarray). The dynamics of circulating antibodies includes both the presence and the absence of an antibody or a plurality of antibodies from the system of a subject. The random sequences allow an unbiased display of all types of antibody binding. The peptides on the microarray serve as mimetics of the actual epitopes and capitalize on the cross-reactivity of antibodies. Even if the actual epitope is not present, another peptide that the same antibody can bind will be present. In addition, the arrays are inexpensive and can be adapted to high-throughput sample processing.

Immunosignatures (IMS) are a merger of microarray and phage technologies that display the complexity of the humoral immune response and convert it into a machine-readable, quantitative format. Immunosignatures are produced by profiling the antibody repertoire of an individual on a chip arrayed with non-natural sequence peptides. It is attractive in that it is a simple but comprehensive measure of the complexity of the humoral response. Immunosignatures detect even tiny perturbations in health status early and accurately. Comprehensive measurements of antibody repertoires provide the means for rapid, inexpensive, and early diagnosis of any diseased state; ultimately, the continuous monitoring of immunosignatures may provide the means to detect dangerous disease states pre-symptomatically.

Generally, immunosignaturing comprises contacting a biological sample (e.g., blood or other bodily sample) with a large number of peptides, nucleic acids, or other biomolecules, where each biomolecule is associated with a feature on a surface. Antibodies in the sample bind differentially to the query molecules at each feature, thus forming a pattern of binding that provides a detailed insight into the molecular recognition profile of the antibodies in the blood. See, e.g., Stafford and Johnston, *Exp. Rev. Aloi. Diagn.* 11:5-8 (2011). Immunosignatures detect and partition an antibody response into a coherent set of signals that can be mathematically interpreted. The concept is that any change in health is likely to be represented by a change in this molecular recognition profile. Such profiles can be used in various analytical methods to further characterize the sample. See for example, U.S. Patent Publication No. 2013/0079242, which is incorporated herein as if set forth in its entirety. Thus, immunosignatures are distinct from and an alternative to traditional, individual protein or genetic biomarkers for the diagnosis of various conditions.

In certain embodiments, the method presented herein comprises contacting a biological sample (e.g., a complex biological sample) of a subject to a peptide array, wherein the peptide array comprises a plurality of peptides capable of off-target binding of at least one antibody in the biological sample; measuring the off-target binding of the antibody to a group of different peptides in the peptide array to form an immunosignature (IMS); and associating the IMS with responsiveness to a particular treatment (e.g., administration of a particular IT) or with a state of health. As used herein, the terms "off-target binding" and "off-target antibody binding" are used interchangeably and refer to unique binding interactions between high affinity monoclonal antibodies and random peptide sequences. The varying strengths of these unique binding reactions can be measured and compared. See U.S. Patent Publication No. 2014/0087963, which is incorporated herein as if set forth in its entirety. See also Halperin et al., Exploring Antibody Recognition of Sequence Space through Random-Sequence Peptide Microarrays. *Molecular & Cellular Proteomics* 10 (2011).

Curiously, many of these off-target mimotope interactions had higher binding than the cognate epitope. Although the corresponding solution-phase binding of these interactions is low, the way the immunosignature microarray is constructed enhances these interactions.

A FS signature is established by using a biological sample (e.g., blood, sera, plasma) that may contain antibodies having affinity to peptides on the FS array. As described herein, antibodies are employed as biomarkers of disease, thus taking advantage of the immune system's expansive antibody repertoire to identify a statistically significant pattern of peptides, each with specific binding values having predictive, prognostic, and diagnostic potential. In some cases, the biological sample is diluted. The sample is incubated long enough to allow cognate binding to approach equilibrium—usually overnight. The array is washed and then incubated with secondary antibody to quantify the amount of antibody bound to each peptide on the array. For each peptide a quantitative amount of fluorescence is determined. These quantitative data can be analyzed in many different analytical and statistical approaches. In general, a patient's FS signature for IT response, prognosis, or side-effects is determined by comparing two or more groups of interest. For example, a comparison may be made between patients who responded well to IT therapy and those that did not. Such comparisons are used to establish the classifier of interest. In some cases, because the FS arrays are directly measuring the immune response to tumor antigens, the difference in groups may be determined directly by quantifying total binding to the FS peptides.

In certain embodiments, the peptide array is a plurality of short linear peptides immobilized on a solid surface (e.g., a polystyrene or other solid substrate). As used herein, the terms "peptide" and "polypeptide" refer to a polymer in which the monomers are alpha amino acids joined together through amide bonds. Peptides are two or often more amino acid monomers long. Standard abbreviations for amino acids are used herein (see Stryer, 1988, Biochemistry, Third Ed., incorporated herein by reference). In certain embodiments, random-sequence peptide arrays are used. As used herein, the term "random peptide" refers to an oligomer composed of two or more amino acid monomers chosen from random sequence space but specifically synthesized. As used herein, the term "random peptide array" includes a set of such peptides as well as a set of fusion proteins containing such random peptides.

In some cases, the peptide array comprises a plurality of human frameshift peptides. In certain embodiments, the frameshift peptides comprise tumor-specific frameshift antigens (molecular targets). In such cases, the methods are useful for determining a subject's responsiveness for IT treatment of a tumor (including early stage tumor formation) associated with a frameshift mutation, which generally arise from mutations in the DNA of coding microsatellite regions or during transcription through microsatellites or mis-splicing. For example, a tumor-associated gene may harbor one or more coding microsatellite regions that, when a mutation occurs that leads to a frameshift with respect to the translational reading frame of the downstream nucleic acid sequence, may give rise to frameshift peptides. Alternatively, when this gene is transcribed a base is inserted or deleted forming a variant RNA that encodes a FS peptide. In addition, FS peptides can be formed through mis-splicing of exons which alter the reading frame.

In some cases, the methods provided herein involve multiplexed arrays in which a plurality of peptides or polypeptides (i.e., proteins) attached to a solid support are contacted to a biological sample (e.g., blood or other bodily tissue obtained from a subject).

Any suitable peptide array can be used on which the peptides are immobilized to a substrate. In some embodiments, the array comprises between 500-1,000,000 peptides; between 500-500,000 peptides; between 500-250,000 peptides; between 500-100,000 peptides; between 500-50,000 peptides; or between 500-10,000 peptides. In some embodiments, the peptides are 8-35, 12-35, 15-25, 10-30, or 9-25 amino acids in length. In some embodiments, the amino acid sequences of the peptides are randomly selected. In some embodiments, the pattern of amino acids present in the microarray is pre-defined (at least in part), and the array is not a random peptide array. In some cases, random-sequence peptide arrays used according to the methods provided herein comprise about 10,000 or more random sequence peptides.

As used herein, the term "substrate" refers to any type of solid support to which the peptides are immobilized. Examples of substrates include, but are not limited to, microarrays; beads; columns; optical fibers; wipes; nitrocellulose; nylon; glass; quartz; diazotized membranes (paper or nylon); silicones; polyformaldehyde; cellulose; cellulose acetate; paper; ceramics; metals; metalloids; semiconductive materials; coated beads; magnetic particles; plastics such as polyethylene, polypropylene, and polystyrene; gel-forming materials; silicates; agarose; polyacrylamides; methylmethracrylate polymers; sol gels; porous polymer hydrogels; nanostructured surfaces; nanotubes (such as carbon nanotubes); and nanoparticles (such as gold nanoparticles or quantum dots). When bound to a substrate, the peptides can be directly linked to the support, or attached to the surface via a linker. Thus, the solid substrate and/or the peptides can be derivatized using methods known in the art to facilitate binding of the peptides to the solid support, so long as the derivitization does not eliminate detection of binding between the peptides and antibodies in the sera.

As used herein, the term "sample" means non-biological samples and biological samples. Non-biological samples include those prepared in vitro comprising varying concentrations of a target molecule of interest in solution. Biological samples include, without limitation, blood, lymph, urine, saliva, sputum, other bodily secretions, cells, and tissue specimens and dilutions of them. Any suitable biological sample can be used. For example, a biological sample can be a specimen obtained from a subject (e.g., a mammal such as a human, canine, mouse, rat, pig, guinea pig, cow, monkey, or ape) or can be derived from such a subject. A subject can provide a plurality of biological sample, including a solid biological sample, from for example, a biopsy or a tissue. In some cases, a sample can be a tissue section or cells that are placed in or adapted to tissue culture. A biological sample also can be a biological fluid such as urine, blood, plasma, serum, saliva, tears, or mucus, or such a sample absorbed onto a paper or polymer substrate. A biological sample can be further fractionated, if desired, to a fraction containing particular cell types. In some embodiments, a sample can be a combination of samples from a subject (e.g., a combination of a tissue and fluid sample). In some cases, sera are obtained from the individual using techniques known in the art.

The methods provided herein are sensitive and involve small quantities of biological samples from a subject. In some embodiments, biological samples from a subject are too concentrated and require a dilution prior to being contacted with an array of the invention. A plurality of dilutions can be applied to a biological sample prior to contacting the sample with an array of the invention. A dilution can be a serial dilution, which can result in a geometric progression of the concentration in a logarithmic fashion. For example, a ten-fold serial dilution can be 1 M, 0.01 M, 0.001 M, and a geometric progression thereof A dilution can be, for example, a one-fold dilution, a two-fold dilution, a three-fold dilution, a four-fold dilution, a five-fold dilution, a six-fold dilution, a seven-fold dilution, an eight-fold dilution, a nine-fold dilution, a ten-fold dilution, a sixteen-fold dilution, a twenty-five-fold dilution, a thirty-two-fold dilution, a sixty-four-fold dilution, and/or a one-hundred-and-twenty-five-fold dilution.

The binding of a molecule to an array in accordance with certain embodiments of the methodology disclosed herein creates a pattern of binding that can be associated with a condition. The affinity of binding of a molecule to a peptide in the array can be mathematically associated with a condition. The off-target binding pattern of an antibody to a plurality of different peptides of the invention can be mathematically associated with a condition. The avidity of binding of a molecule to a plurality of different peptides can be mathematically associated with a condition. The off-target binding and avidity can comprise the interaction of a molecule in a biological sample with multiple, non-identical peptides in a peptide array. An avidity of binding of a molecule with multiple, non-identical peptides in a peptide array can determine an association constant of the molecule to the peptide array. In some embodiments, the concentration of an antibody in a sample contributes to an avidity of binding to a peptide array, for example, by trapping a critical number or antibodies in the array and allowing for rapid rebinding of an antibody to an array.

The peptide array can be contacted with the biological sample (e.g., sera) under any suitable conditions to promote binding of antibodies in the sample to peptides immobilized on the array. Thus, the methods presented herein are not limited by any specific type of binding conditions employed. Such conditions will vary depending on the array being used, the type of substrate, the density of the peptides arrayed on the substrate, desired stringency of the binding interaction, and nature of the competing materials in the binding solution. In a certain embodiments, the conditions comprise a step to remove unbound antibodies from the addressable array.

Similarly, any suitable detection technique can be used in the methods provided herein to detect binding of antibodies in the biological sample to peptides on the array to generate a subject's immunosignature or FS signature. In one embodiment, any type of detectable label can be used to label peptides on the array, including but not limited to radioisotope labels, fluorescent labels, luminescent labels, and electrochemical labels (i.e., ligand labels with different electrode mid-point potential, where detection comprises detecting electric potential of the label). Alternatively, bound antibodies can be detected, for example, using a detectably labeled secondary antibody.

The composition of molecules in an array can determine an avidity of binding of a molecule to an array. A plurality of different molecules can be present in an array used to predict a subject's responsiveness to a particular treatment. Non-limiting examples of biomolecules include amino acids, peptides, peptide-mimetics, proteins, recombinant proteins antibodies (monoclonal or polyclonal), antibody fragments, antigens, epitopes, carbohydrates, lipids, fatty acids, enzymes, natural products, nucleic acids (including DNA, RNA, nucleosides, nucleotides, structure analogs or combinations thereof), nutrients, receptors, and vitamins. In some embodiments, a molecule in an array is a mimotope, a molecule that mimics the structure of an epitope and is able to bind an epitope-elicited antibody. In some embodiments, a molecule in the array is a paratope or a paratope mimetic, comprising a site in the variable region of an antibody (or T-cell receptor) that binds to an epitope of an antigen. In some embodiments, an array employed in accordance with the methodologies presented herein is a peptide array comprising random peptide sequences or known frameshift peptides.

In certain embodiments, the subject has been diagnosed with cancer or other cell proliferative disorder. As used herein, the term "cancer" refers to the broad class of disorders characterized by hyperproliferative cell growth, either in vitro (e.g., transformed cells) or in vivo. Cancers appropriate for treatment with checkpoint inhibitor therapy include without limitation a variety of neoplasms, including benign or malignant tumors, a variety of hyperplasias, and the like. Non-limiting examples of cancers that can be diagnosed, monitored, prevented, and/or treated with an array and a method of the invention can include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstr6m macroglobulinemia, and Wilms tumor. The cancer could be diagnosed by an IMS or FS signature, even at a very early stage.

As used herein the term "immunotherapeutic" or "IT" refers to a compound that is used to, in this case, treat cancer by inducing, enhancing or suppressing the immune response. Immunotherapeutics encompass immune checkpoint inhibitors, antibody-drug conjugates (ADCs), monoclonal antibodies, T-cell therapy, small molecules, and bispecific antibodies (bsAbs). Antibody-drug conjugates include monoclonal antibodies linked to biologically active drugs to combine the targeting ability of antibodies as well as the cytotoxic ability of the drug. T-cell therapy involves reprogramming a patient's own immune T-cells to attack tumors. One type of well-known T-cell therapy comprises adoptive transfer of chimeric antigen receptor (CAR) T-cells. As used herein, the term "chimeric antigen receptor" refers to a fusion protein of the membrane or intracellular signaling region of T-cell activating proteins (e.g., CD3-zeta chain, CD28, 41BBL, OX40, ICOS, high-affinity receptor for IgE (FcεRI) and other T-cell activating proteins) and the antigen-binding site (i.e., single-chain Fv fragment) of a cancer antigen-specific antibody. Bispecific antibodies are recombinant proteins that can bind to two different types of antigen at the same time. For example, a bsAb can be engineered to bind a cytotoxic cell and a target tumor cell. That way, the bsAb brings the cytotoxic cell and the target tumor cell into close proximity and facilitates tumor treatment.

In certain embodiments, the immunotherapeutic is selected from Tremelimumab (CTLA-4 blocking antibody), OX40 agonists (e.g., agonist antibodies), antibodies to B7 ligands (e.g., anti-B7-H1, anti-B7-H3, anti-B7-H3, anti-B7-H4), durvalumab (MEDI4736, anti-PD-L1 antibody), MK-3475 (PD-1 blocker), Nivolumab (anti-PD-1 antibody), Pembrolizumab (anti-PD-1 antibody), Pidilizumab/CT-011, BY55 monoclonal antibody, AMP224 (anti-PD-L1 antibody), BMS-936559 (anti-PD-L1 antibody), MPLDL3280A (anti-PD-L1 antibody), MSB0010718C (anti-PD-L1 antibody), and Yervoy/ipilimumab (anti-CTLA-4 checkpoint inhibitor). Many new inhibitor targets are being investigated. In some cases, IT treatment comprises a combination therapy in which two or more immunotherapeutics are administered.

As used herein the terms "checkpoint inhibitor" and "checkpoint pathway inhibitor" are used interchangeably and refer to negative regulatory molecules, usually antibodies, that block or inhibit anti-T-cell anti-tumor function to enhance tumor killing. Checkpoint inhibitors include, without limitation, CTLA-4, PD-L1, PD-L2, PD-1, B7-H3, B7-H4, BTLA, HVEM, TIM3, GAL9, LAG3, VISTA, KIR, 2B4, CD160, CGEN-15049, CHK 1, CHK2, A2aR, and a B-7 family ligand such as B7-1, B7-2, B7-DC, B7-H1, B7-H2, B7-H3, B7-H4, B7-H5, B7-H6 and B7-H7 (or any combination thereof), or a combination thereof (e.g., a combination of CTLA-4 and PD-L1 or PD-L2).

Figure 11:
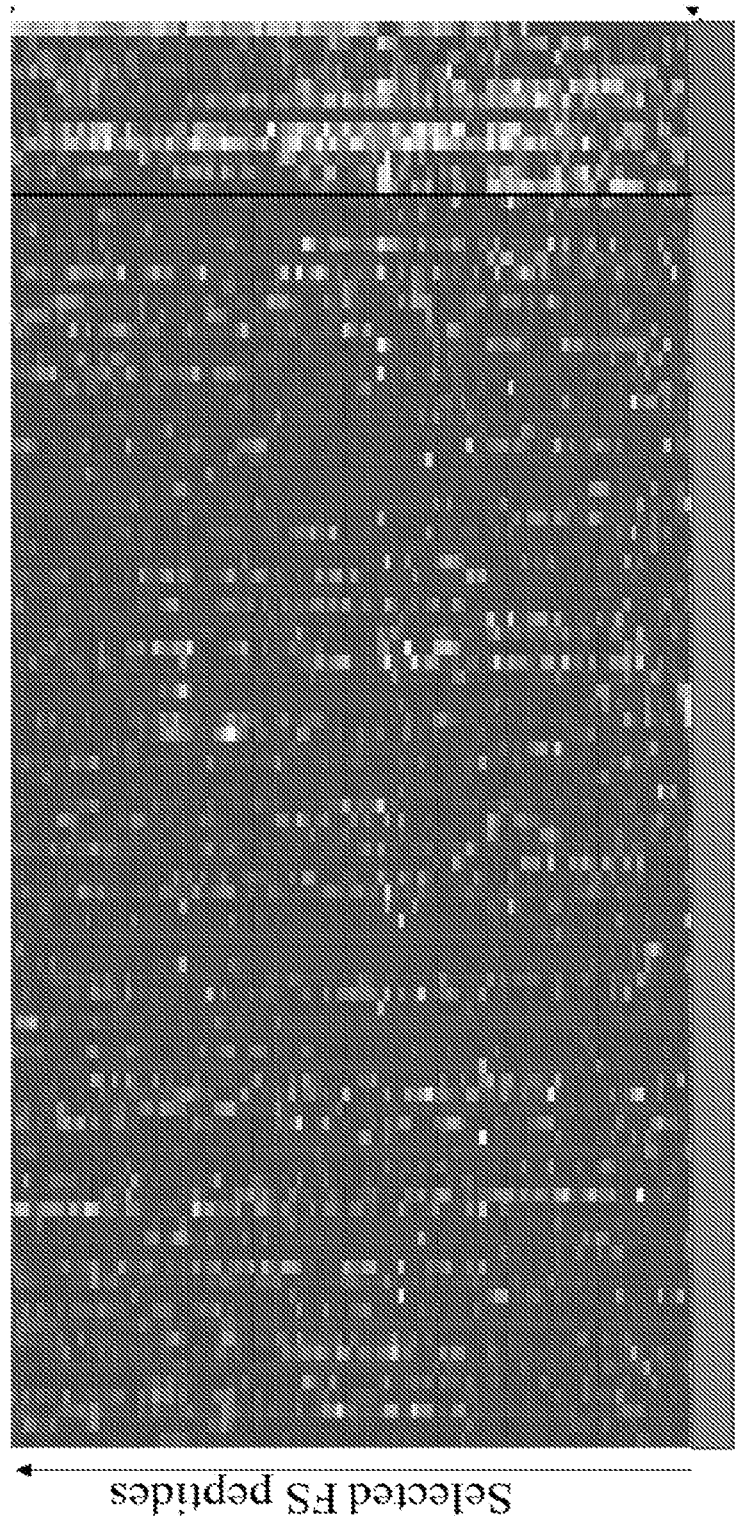
FIG. 11 is a heat-map demonstrating that FS peptide signatures can distinguish the patients likely to experience serious side-effects (blue) under IT treatment from the "no side-effect" patients (red). Significant FS peptides were selected by comparing side-effect patients and no side-effect patients. Heat-map shows that the selected FS peptides cluster the side effect patients with 100% accuracy.
Figures 12A, 12B:
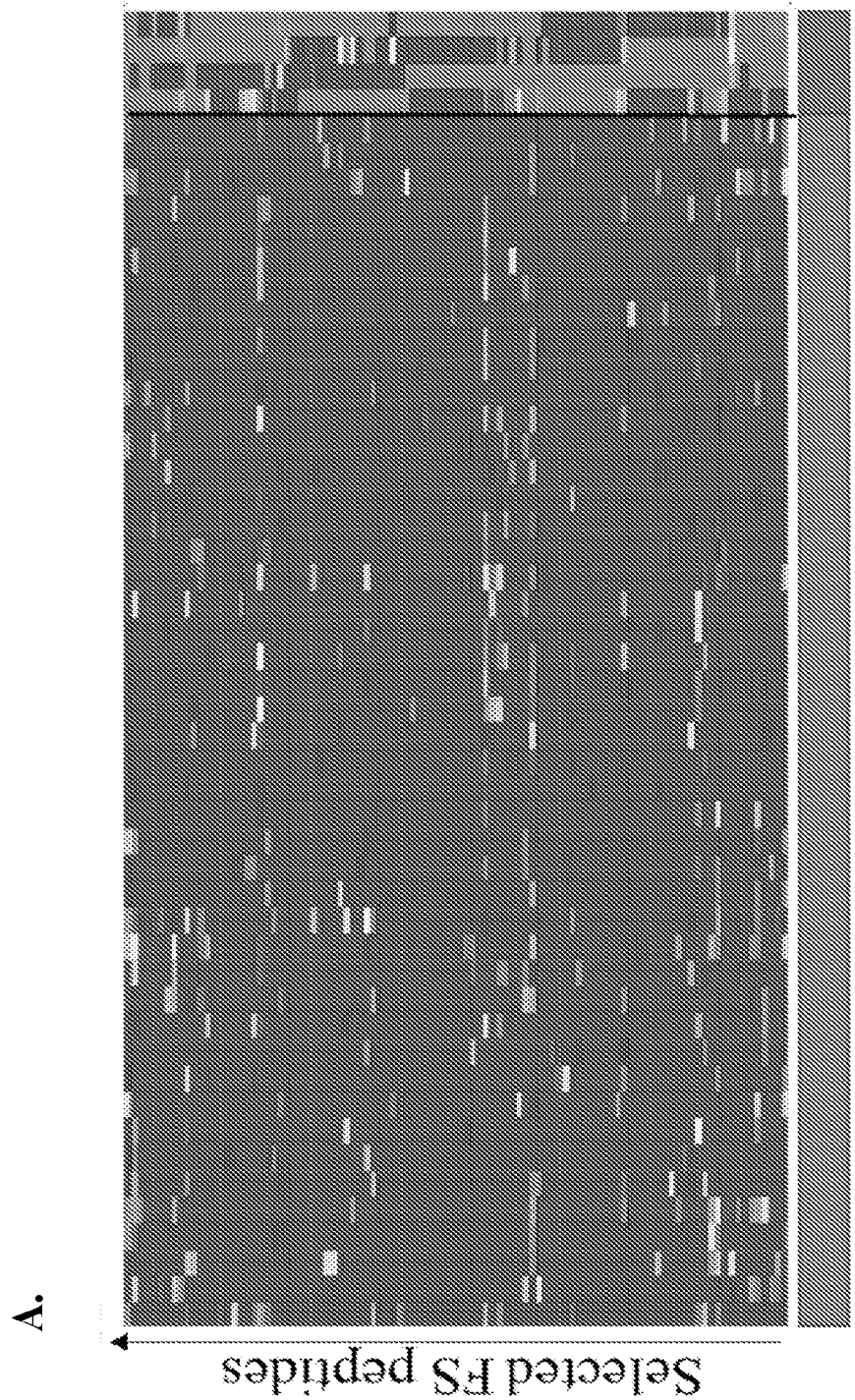
FIGS. 12A-12B demonstrates that FS peptide arrays can distinguish patients likely to have a serious side-effect (blue) under IT treatment from the "no side effect" patients (red). Significant FS peptides were selected by comparing side-effect patients and no-side effect patient patients. Both heat-map (A) and Principle Component Analysis (B) demonstrated that the selected FS peptides cluster the side effect patients with 100% accuracy.

As used herein, the term "side effect" or "side effects" refers to the unacceptable or undesirable adverse symptoms resulting from or associated with the administration of a particular treatment such as an IT therapy. Side effects specifically to immunotherapeutics are termed "immune related adverse events" (irAE). While side effects vary by the type of therapy, common side effects of IT therapies include, without limitation fatigue, infusion related reactions, dermatological toxicity, diarrhea/colitis, hepatotoxicity, pneumonitis, hyper- and hypo-thyroidism. For review, see e.g., uptodate.com/contents/patient-selection-criteria-and-toxicities-associated-with-checkpoint-inhibitor-immunotherapy on the World Wide Web. Immune-related adverse events are generally graded from 1-4. Grades 3 and 4 are considered serious and can require immunosuppression treatment. Patients with irAE are just as likely to have a positive response to treatment. Occurrence of Grade 3 or 4 event can prohibit the patient from further IT therapy. Therefore, knowing ahead of time which patients are more likely to have an event would allow closer monitoring to pre-empt a Grade 3 or 4 event. The irAE patients in FIG. 11 experienced grade 2 or higher events (e.g., hypothyroidism, diarrhea, elevated ALT/AST (hepatotoxicity), colitis, diabetes, rash, fatigue). It is of note that, even though they suffered from a variety of events, they had a common predictive signature. Patients associated with samples reported in FIG. 11 suffered from grade 2 or higher events such as hypothyroidism, diarrhea, elevated ALT/AST (hepatotoxicity), colitis, diabetes, rash, and fatigue.

Any appropriate criteria can be used to confirm a subject's responsiveness to treatment with an IT. For example, in certain embodiments, responsiveness to treatment by an IT is measured by at least one criterion selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

The methods described herein can be carried out using a computer programmed to receive data (e.g., data from a random or FS peptide array indicating whether a subject has a signature associated with responsiveness to IT therapy). The computer can output for display information related to a subject's biomarkers, and the likelihood of the duration of time that the subject will be responsive to an IT therapy, suffer a side-effect, or the prognosis of survival.

After information regarding a subject's biomarkers is reported, a professional can take one or more actions that can affect patient care (e.g., administer a new treatment or modify an existing treatment). For example, a medical professional can record the information in a subject's medical record and/or in an electronic database. In some cases, a medical professional can record that the subject is likely or not likely to respond to an IT therapy, or otherwise transform the patient's medical record, to reflect the patient's medical condition. In some cases, a medical professional can review and evaluate a patient's medical record, and can assess multiple treatment strategies for clinical intervention of a patient's condition. The signature may indicate watchfulness or pre-treatment for a side-effect or recommendation for a different treatment.

A professional (e.g., medical professional) can communicate information regarding biomarker analysis to a subject or a subject's family. In some cases, a professional can provide a subject and/or a subject's family with information regarding an IT therapy, including treatment options and potential side effects. In some cases, a professional can provide a copy of a subject's medical records to communicate information regarding biomarker analysis and/or disease states to a specialist.

A professional (e.g., research professional) can apply information regarding a subject's biomarkers to advance research into IT therapy. For example, a researcher can compile data on the presence of a particular signature with information regarding the efficacy of an IT therapy, or side effects associated with an IT therapy. In some cases, a research professional can obtain a subject's biomarker information to evaluate the subject's enrollment, or continued participation in a research study or clinical trial. In some cases, a research professional can communicate a subject's biomarker information to a medical professional, or can refer a subject to a medical professional for clinical assessment and/or treatment.

Any appropriate method can be used to communicate information to another person (e.g., a professional), and information can be communicated directly or indirectly. For example, a laboratory technician can input biomarker information into a computer-based record. In some cases, information can be communicated by making a physical alteration to medical or research records. For example, a medical professional can make a permanent notation or flag a medical record for communicating information to other medical professionals reviewing the record. Any type of communication can be used (e.g., mail, e-mail, telephone, and face-to-face interactions). Information also can be communicated to a professional by making that information electronically available to the professional. For example, information can be placed on a computer database such that a medical professional can access the information. In addition, information can be communicated to a hospital, clinic, or research facility serving as an agent for the professional.

Articles of Manufacture

This disclosure also provides articles of manufacture that can include, for example, materials and reagents that can be used to determine whether a subject has a biomarker for predicting response to an IT treatment. An article of manufacture can include, for example, peptides, nucleic acids, or polypeptides immobilized on a substrate (e.g., in discrete regions ("features") with different populations of isolated peptides, nucleic acids, or polypeptides immobilized in each discrete region) such as in a nucleic acid array. The article of manufacture can also include instructions for use in practicing a method for predicting the likelihood of a subject responding to an IT treatment as provided herein.

The article of manufacture may further comprise one or more nucleic acid arrays or peptide arrays for performing the analysis. In some cases, the nucleic acid arrays and peptide arrays are attached to a solid substrate, e.g., a porous or non-porous material that is insoluble. The nucleic acids or peptides of each array can be immobilized on the substrate covalently or non-covalently.

Also provided are kits containing any of the nucleic acid arrays described herein. The kits can optionally contain instructions for detecting one or more signatures described herein. The kits can optionally include, e.g., a control biological sample or control labeled-amplicon set containing known amounts of one or more amplicons recognized by nucleic acid probes of the array.

In some cases, one or more reagents for processing a biological sample and/or using the arrays (e.g., reducing reagents, denaturing, deglycosylating reagents, dephosphorylating reagents, alkylating reagents and/or reagents for chemically or enzymatically cleaving a peptide or protein) are provided with the kit. A kit also can include a detection reagent for detecting the presence or absence of a particular signature. Alternatively, such reagents may be provided separately from the kit.

In some cases, the kits can include a software package for analyzing the results of, e.g., a peptide array analysis, immunosignaturing, or FS array analysis.

Instructions for the above-described articles of manufacture are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub packaging), etc. In other embodiments, the instructions are present as an electronic storage data file present on a suitable computer readable storage medium, e.g., CD-ROM, diskette, etc., including the same medium on which the program is presented.

In yet other embodiments, the instructions are not themselves present in the kit, but means for obtaining the instructions from a remote source, e.g., via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or World Wide Web. Some form of access security or identification protocol may be used to limit access to those entitled to use the subject invention. As with the instructions, the means for obtaining the instructions and/or programming is generally recorded on a suitable recording medium.

The kits described herein also can optionally include instructions for treating a cancer patient based on the presence or absence of a signature as described herein.

"Determining," "measuring," "assessing," "assaying" and like terms are used interchangeably and can include both quantitative and qualitative determinations. Assessing may be relative or absolute. "Assessing the presence of" includes determining the amount of something present, as well as determining whether it is present or absent.

Note that as used herein and in the appended claims, the singular forms "a," "an," and "the" include plural referents unless the context clearly dictates otherwise. Thus, for example, reference to "an array" refers to one or more such arrays, and reference to "the method" includes reference to equivalent steps and methods known to those skilled in the art, and so forth.

It is contemplated that any embodied method or composition described herein can be implemented with respect to any other method or composition described herein.

As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Although the embodiments are described in considerable detail with reference to certain methods and materials, one skilled in the art will appreciate that the disclosure herein can be practiced by other than the described embodiments, which have been presented for purposes of illustration and not of limitation. Therefore, the scope of the appended claims should not be limited to the description of the embodiments contained herein.

Certain embodiments of the invention are further described in the following example, which does not limit the scope of the invention described in the claims but rather is included to demonstrate such embodiments. It should be appreciated by those of skill in the art that the techniques disclosed in the examples which follow represent techniques developed by the inventors to function well in the practice of the methods provided herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1—Classifying Responders to Combination Immunotherapy Treatments

Figure 3B:
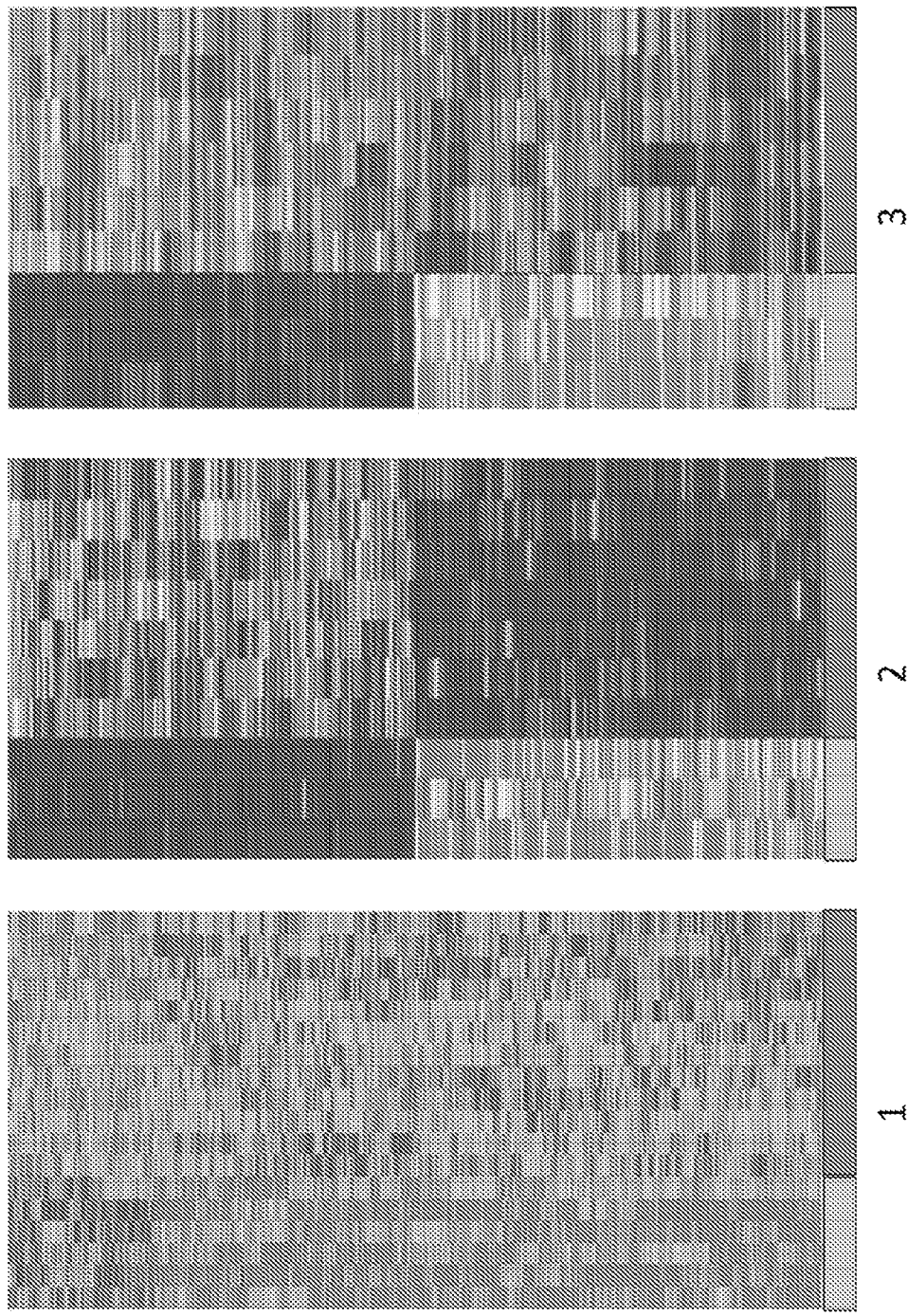

As shown in FIGS. 3A-3B, IMS can distinguish responders to anti-PDL1 and anti-CTLA4 combination treatment from non-responders in a mouse model of osteosarcoma lung metastasis. Following intravenous (i.v.) injection of cells of the K7M2 osteosarcoma cell line, the mice were treated with 3 dosages of anti-PDL1 plus anti-CTLA4, and 2 additional dosages of anti-PLD1 treatment. Treatments were spaced three days apart. IMSs were analyzed at the following time-points: (1) prior to the tumor injection and the treatment, (2) right after the treatment, and (3) at the end of the experiment when non-responder mice have died from lung metastasis. At each time point, IMS significantly distinguished the responder mice from the non-responder mice. Remarkably, IMS could predict the response even before the tumor was injected.

Further study of IT response prediction was performed using a mammary tumor mouse model and either an IMS or FS peptide array. The 4T-1 mammary tumor cell line was used. Four groups of mice were assayed. Group 1: No Treatment (28 mice). Group 2: Early treatment group (1$^{st}$ treatment at 16 weeks) (16 mice). Group 3: Treat at first palpable tumor (1$^{st}$ treatment at ~33 weeks). Group 4: Late treatment group (1st treatment at 24-26 weeks) (15 mice). IT treatment was 100 μg anti-CTLA4 (UC10-4F10-11) plus 200 μg anti-PD-L1 (10F.9G2). Five doses were administered, with each dose administered every 3 days, and then two additional doses, with one every week. Palpable tumors were monitored following the treatment period.

Figure 4:
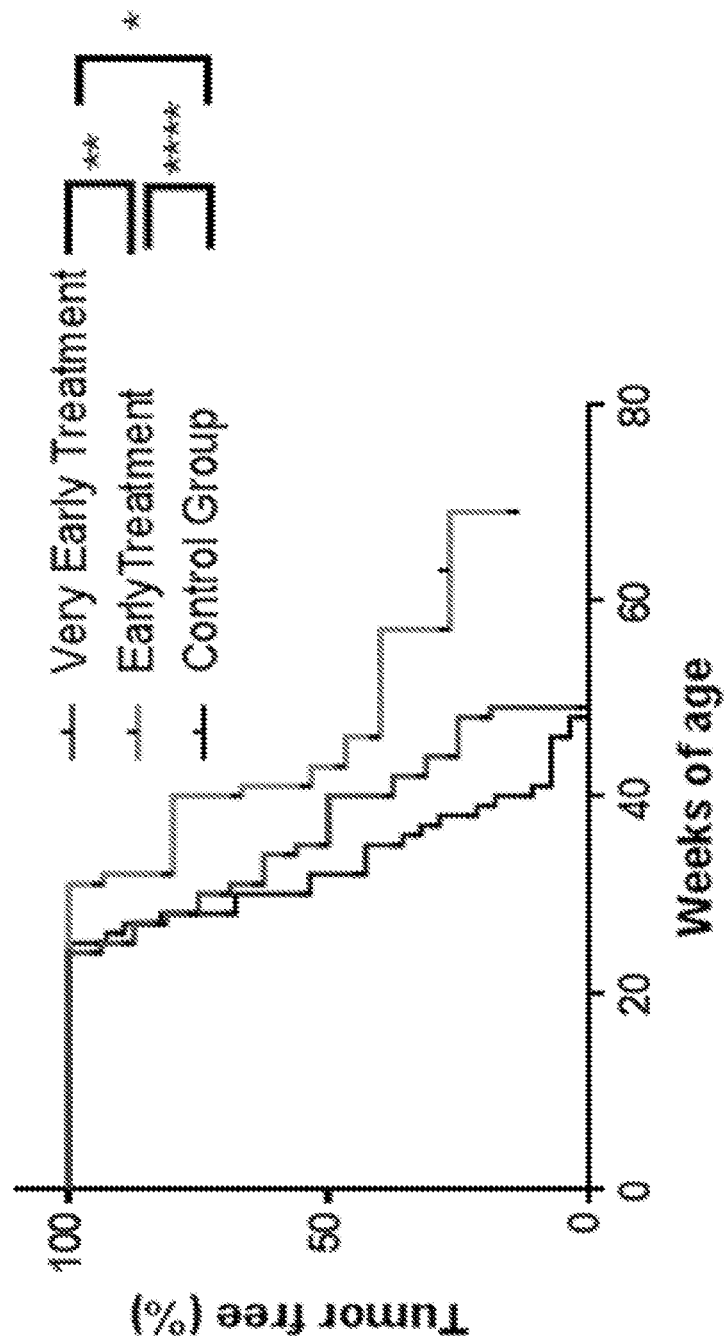
FIG. 4 is a graph demonstrating the percentage tumor-free mice per treatment group over time. Non-treatment group: no treatment before palpable tumor (28 mice). Early treatment group: 16 mice; late treatment group: 15 mice. Non-treatment vs Early treatment: p-value=0.0322; Non-treatment vs Late treatment: p-value=0.0003.

As shown in FIG. 4, palpable tumor initiation was significantly delayed by very early IT treatment and early treatment. Late IT treatment had no effect (data not shown). These results are presented in Table 1.

TABLE 1

Responder vs Non-responder in Early Treatment Group

| Mouse | Tumor Initiation Age (weeks) | Type |
|---|---|---|
| ET5-6 | 23.7 | Non-responder |
| ET5-3 | 24.7 | Non-responder |
| ET3-2 | 27.14 | Non-responder |
| ET2-2 | 27.57 | Non-responder |
| ET3-3 | 30.14 | Non-responder |
| ET1-3t | 30.86 | Non-responder |
| ET3-6 | 33.57 | Non-responder |
| ET2-8 | 41.57 | Responder |
| ET2-10 | 47.57 | Responder |
| ET3-8 | 48.57 | Responder |
| ET1-5 | 48.86 | Responder |
| ET1-8 | 48.86 | Responder |

Figure 5:
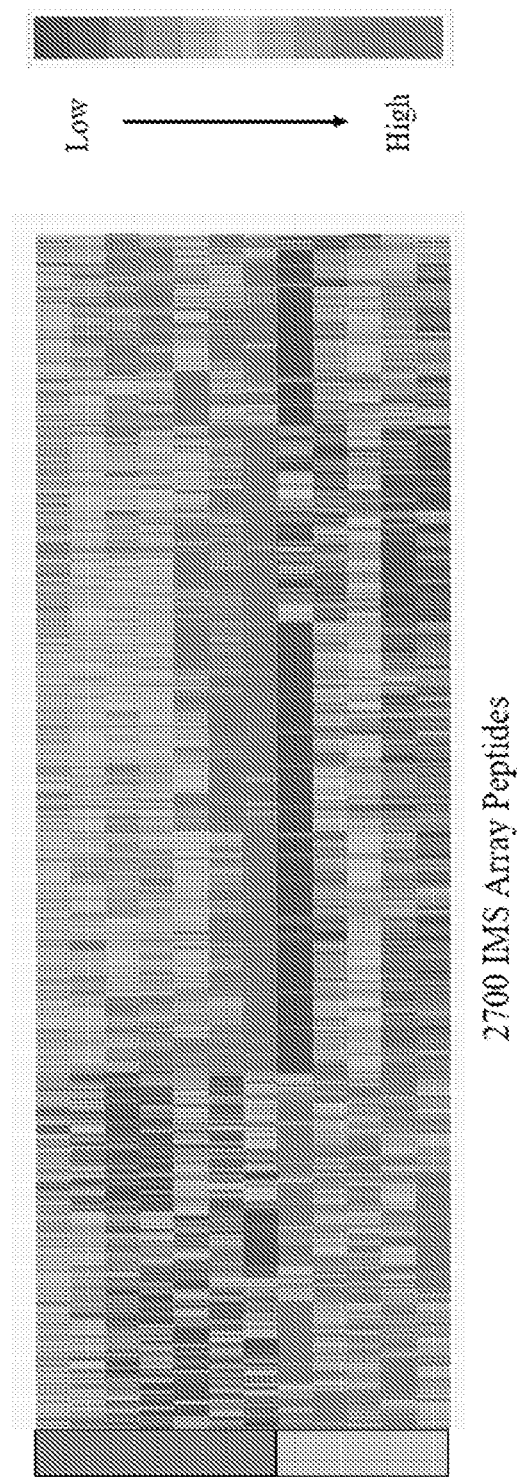
FIG. 5 is a heat-map demonstrating hierarchical clustering of 120,000 immunosignatures (IMS) for responders (green bar) vs non-responders (red bar) in the early treatment group.
Figure 6:
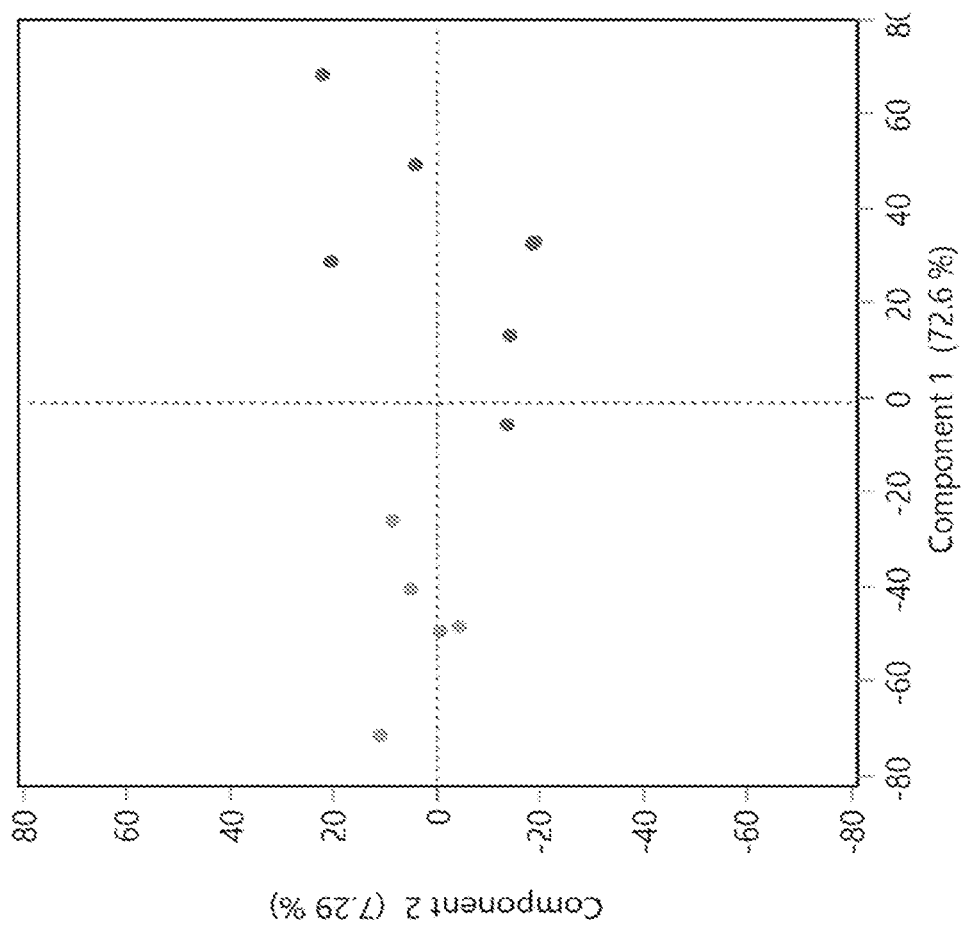
FIG. 6 is a graph presenting Principle Component Analysis (PCA) data for responder and non-responder groups. Green dots: Responder; Red dots: Non-responder.
Figure 7:
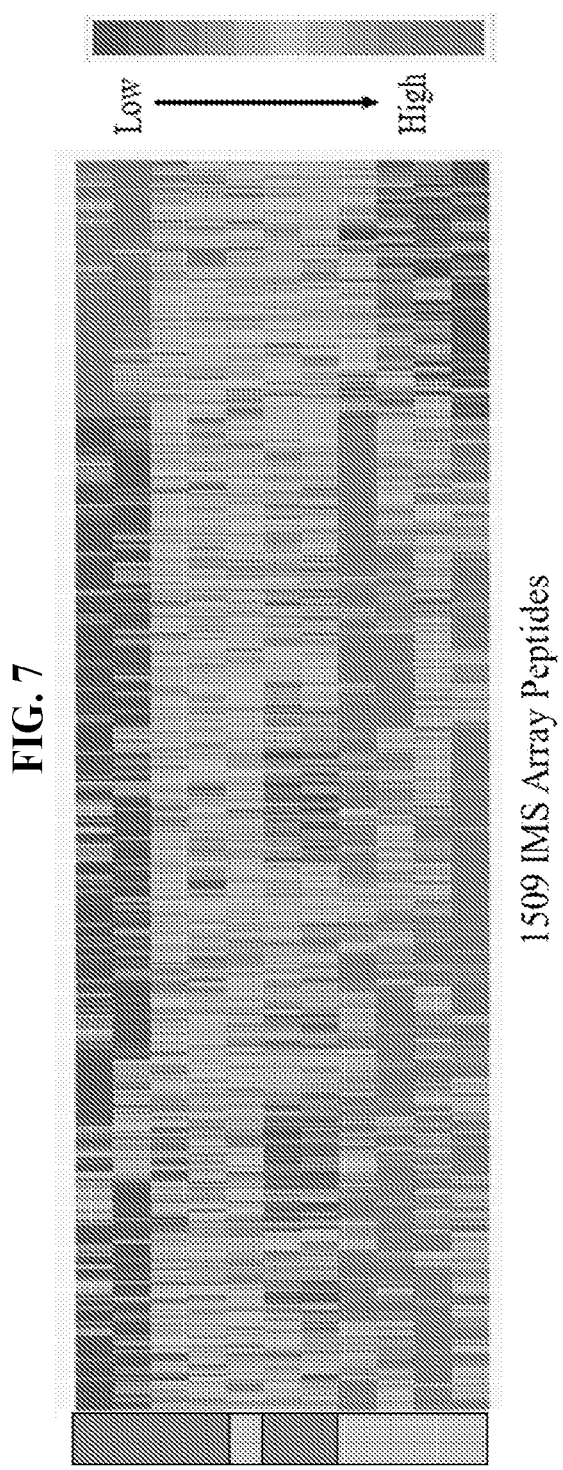
FIG. 7 demonstrates hierarchical clustering of peptides distinguishing early (red bar) and late tumor (green bar) events in the non-treatment group. Only one late tumor event was misclassified. This indicates that an IMS can distinguish the course of a tumor (prognosis) regardless of treatment.

IMS from 120K peptide arrays were obtained for responders and non-responders in the early treatment group. As shown in FIGS. 5 and 6, 2700 peptides (selected by T-test) distinguished responders from non-responders in the early treatment group. It was further determined that the same 2700 peptides could distinguish early tumor events and late tumor events in the non-treatment group (see FIG. 7 and Table 2). This indicates that IMS arrays can distinguish the course of a tumor (prognosis) regardless of treatment.

TABLE 2

Early Tumor vs Late Tumor in Non-Treatment Group

| Mouse | Tumor Initiation Age (weeks) | Type |
|---|---|---|
| NT3-7 | 24.57 | Early Tumor |
| NT1-2 | 25.14 | Early Tumor |
| NT4-6 | 26.14 | Early Tumor |
| TT5-4 | 27.14 | Early Tumor |
| TT5-6 | 27.14 | Early Tumor |
| TT3-5 | 27.57 | Early Tumor |
| NT3-3 | 39.57 | Late Tumor |
| TT4-3 | 39.57 | Late Tumor |
| NT1-Tat | 40.71 | Late Tumor |
| TT2-2 | 45.86 | Late Tumor |
| TT2-6 | 47.86 | Late Tumor |

Figure 8:
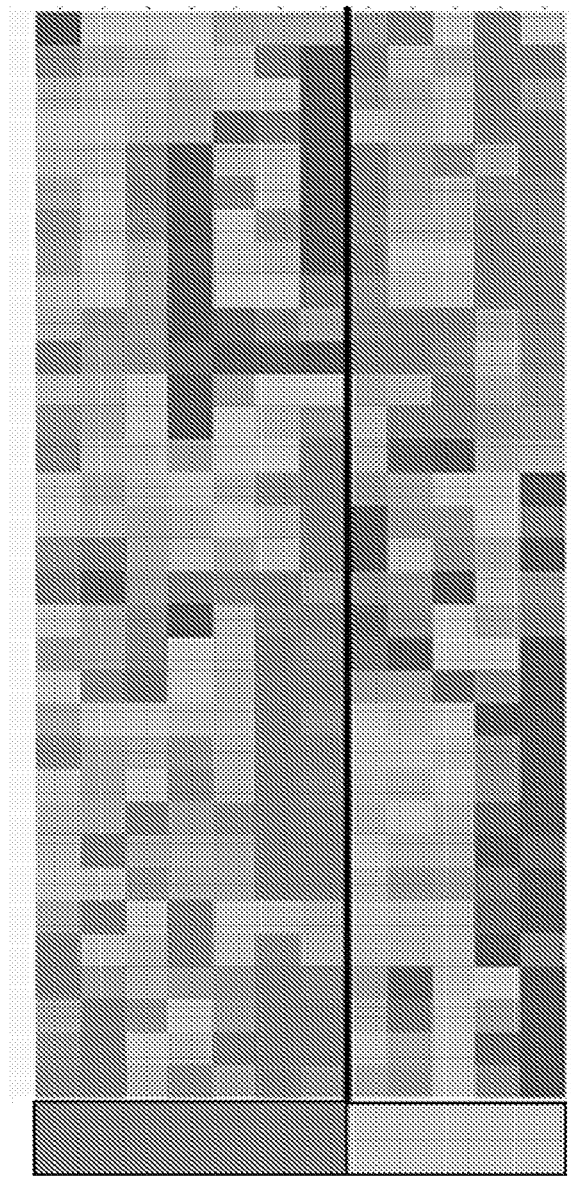
FIG. 8 demonstrates hierarchical clustering of peptide distinguishing Responders (green bar) vs Non-responders (red bar) in the early treatment group using 33 significant FS peptides from an 800 FS peptides array.

We also analyzed the same subjects (Responders versus Non-Responders) from the Early Treatment group on an 800-peptide, spotted FS array. As shown in FIG. 8, hierarchical clustering revealed 33 significant FS peptides from the 800-peptide FS array capable of distinguishing Responders (green bar) from Non-responders (red bar) in the early treatment group. These data demonstrate that, like IMS, FS peptide signatures are also able to distinguish Responders from Non-Responders.

Figure 9:
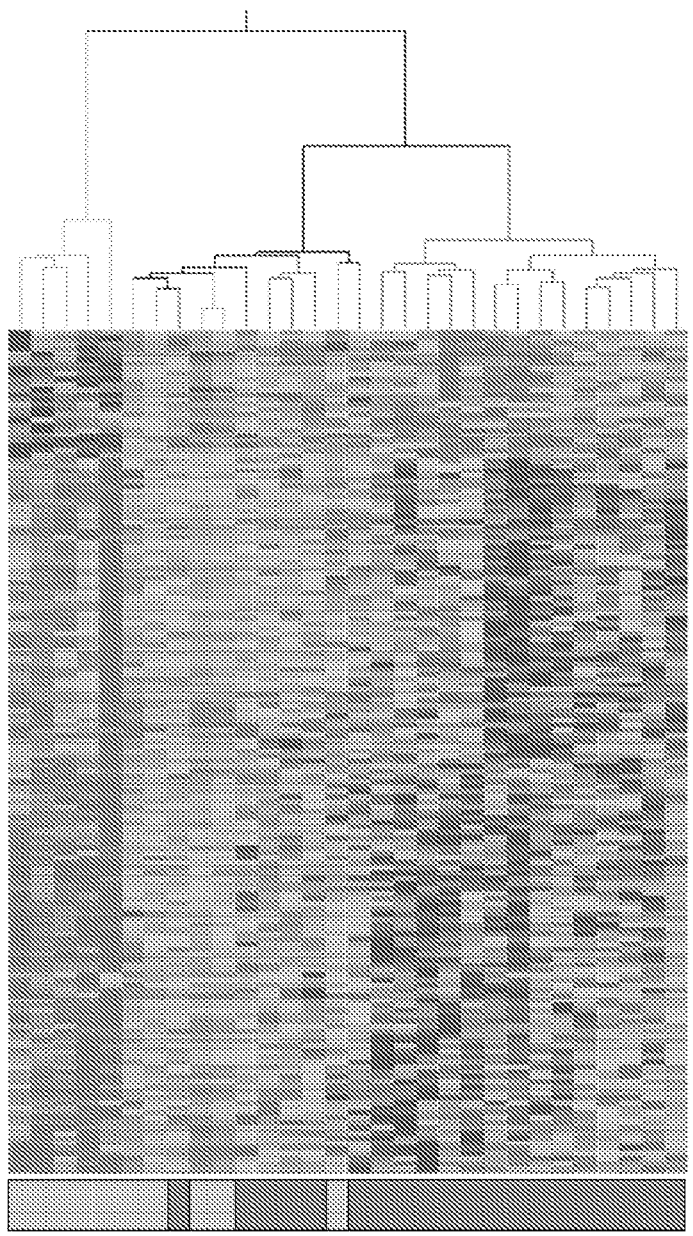
FIG. 9 that the IMS can be used to distinguish human cancer patients that responded (n=10, green bar) or did not (n=20, red bar) to IT treatment. Leave one out validation shows about 79% accuracy to predict the responder to the IT treatment.
Figure 10A:
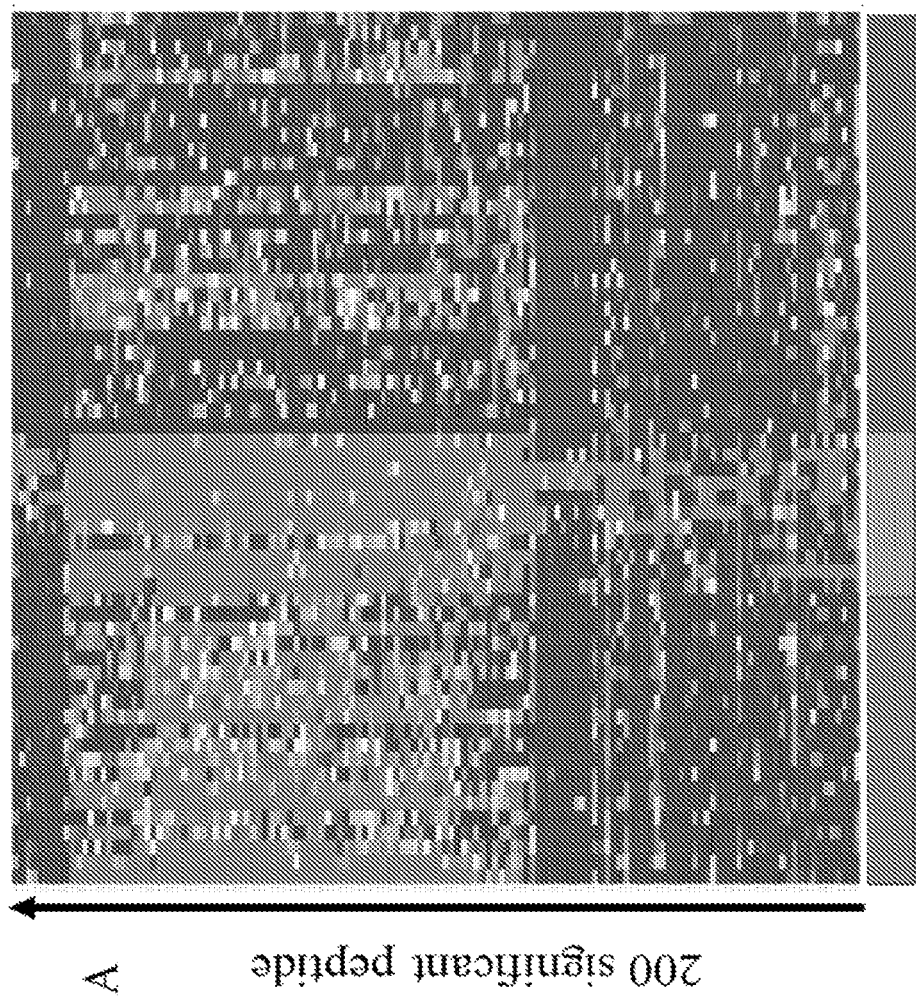
FIGS. 10A-10D demonstrate that FS peptide signatures can be used to distinguish the responses of human cancer patients to IT treatment. Serum samples from responders (n=10, green bar), non-responders (n=20, red bar) and 20 healthy subjects (n=20, blue bar) were applied to a FS peptide array. Each panel uses a different classification method. (A). Selection of 200 most significantly higher IgG reactive FS peptides in responders based on t-test by comparing to non-responders could cluster responders and non-responders. Leave one out validation with SVM shows 96.6% accuracy to predict the responder to the IT treatment. (B). Using the total relative fluorescence units (RFU) of the selected 200 significant FS peptides to predict the responder. The total RFU greater than 1,000, is the responder (green bar); which the total RFU less than 400, is the non-responder (red bar) or healthy subject (blue bar). The accuracy of leave-one-out validation of this method is 96%. (C). Cluster the responder (green bar) and non-responder (red bar) by highly positive reactive FS peptide. Positive cut-off value was calculated by average of the non-responders plus 6 fold of the standard deviation of the non-responders. Selection of the top 500 positive peptides in responders can cluster 100% accuracy of the responders and non-responders. (D). Using the positive peptide number to predict the responder patients to the IT treatment. Total positive peptide number was counted of each sample from the top 500 positive rate FS peptides of the responders. Positive cut-off value was calculated by average of the non-responders (NR) plus 6 fold of the standard deviation of the non-responders. 20 rounds leave-one-NR-out validation decided the cut-off positive peptide number for responder is 79 (average plus 95% CI of the NR positive peptide number). The average accuracy to predict the responder is 97.3%. Error bar is 95% CI.
Figure 10B:
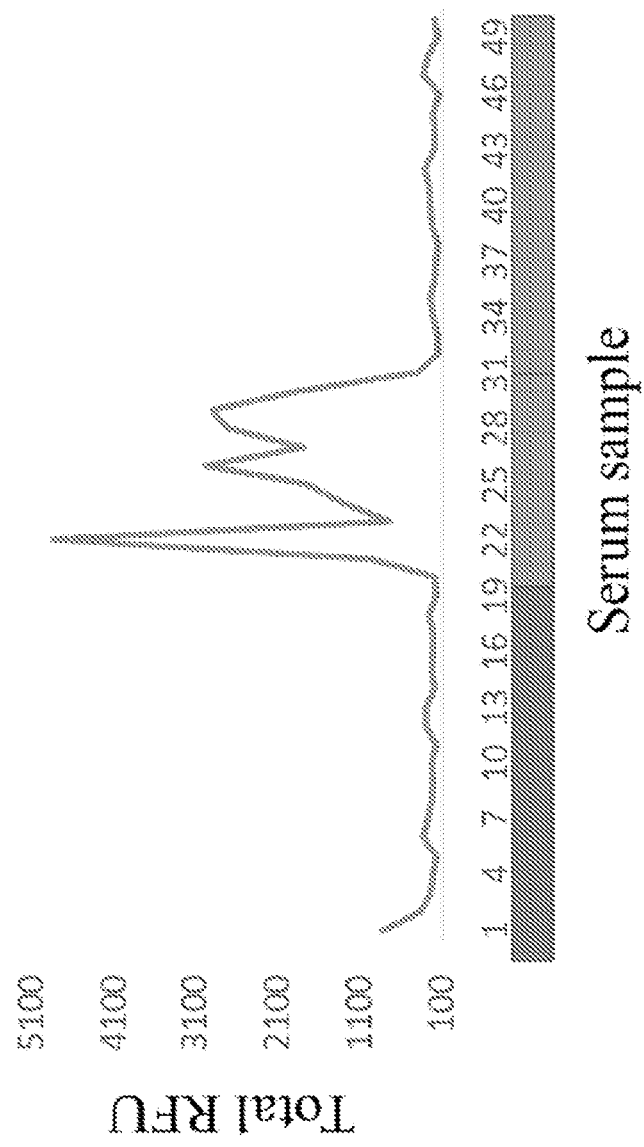
Figure 10C:
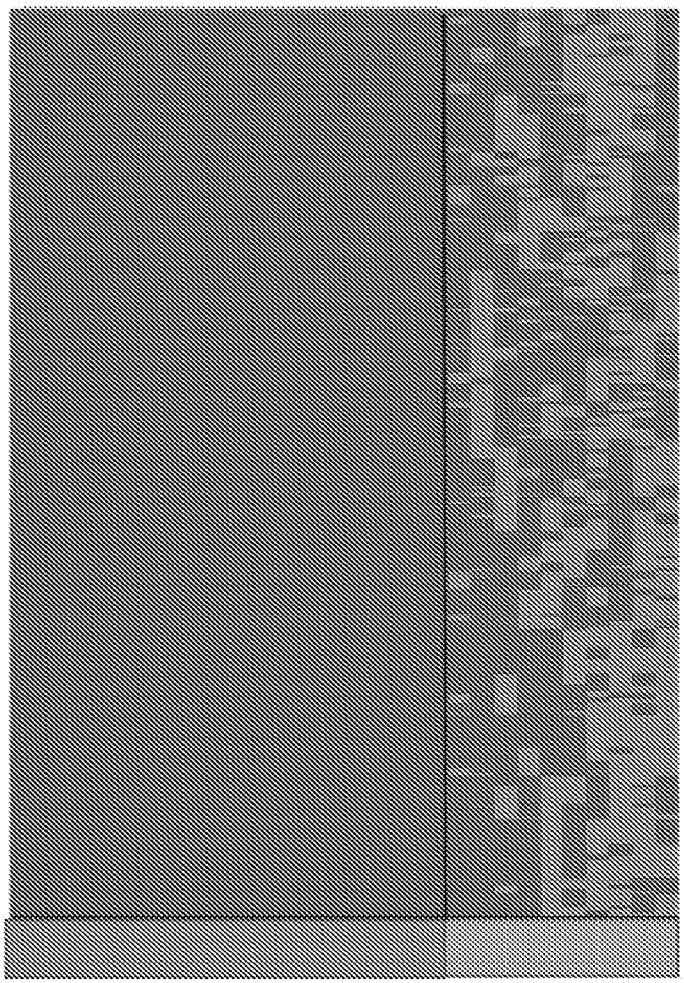
Figure 10D:
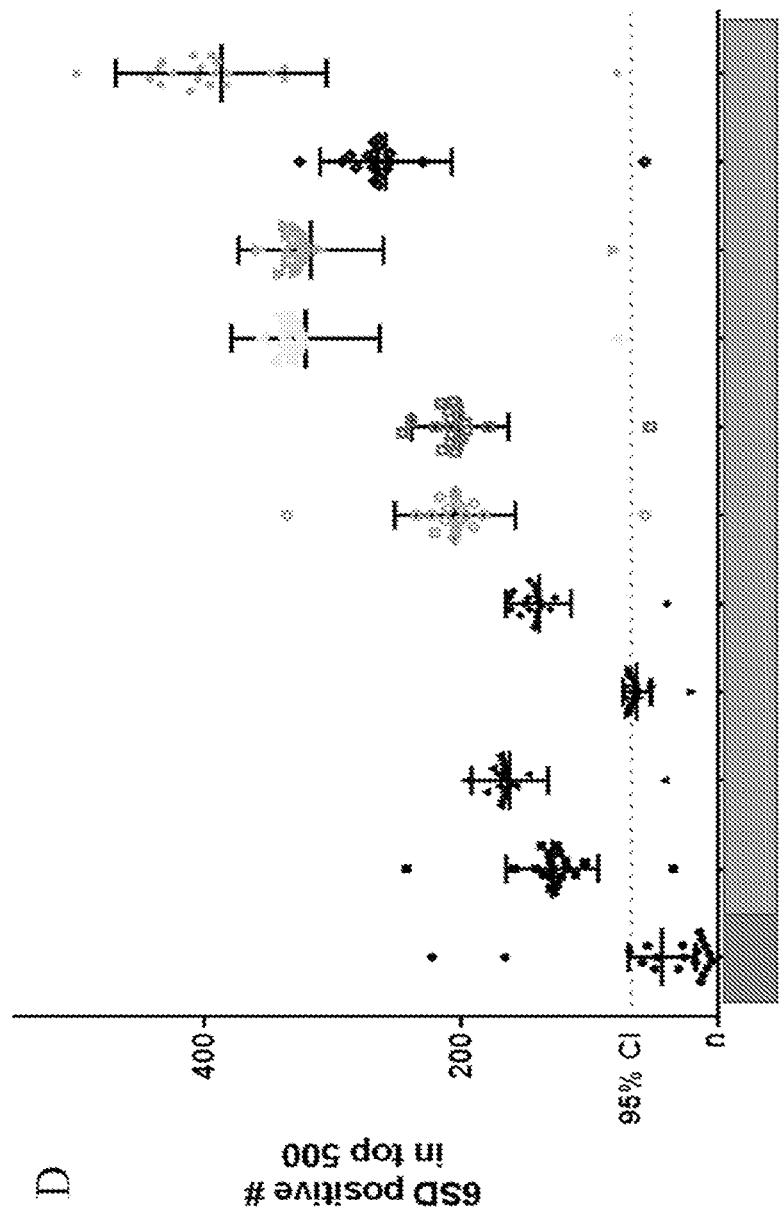

Example 2—Distinguishing Human Responders and Non-Responders to PD-1 Treatment Using IMS and FS Peptide Signatures 78 blood samples were obtained from MD Anderson. The samples were obtained from human patients having various cancers that were being treated with an immunotherapeutic agent that inhibits PD-1. The samples were obtained before treatment started. At the time of the IMS/FS assay, 30 patients had been monitored long enough to be designated as "Responder" or "Non-Responder" to PD-1 inhibitor treatment. All 78 samples were analyzed on the IMS arrays. As shown in FIG. 9, IMS can be used to distinguish human cancer patients that responded (n=10, green bar) or did not (n=20, red bar) to IT treatment. Leave one out validation revealed about 79% accuracy to predict responders to the IT treatment. The same set of 30 samples were also analyzed on FS arrays with 400K peptides. These arrays were even better at distinguishing the Responders from Non-Responders. Different types of analysis applied to the FS data yielded different accuracies (FIGS. 10A-10D). Based on this data, a physician could take a small sample of blood from a patient before treatment and determine with high accuracy whether the patient was likely to respond to that particular therapy. If the likelihood was low, a different therapy could be recommended. If the patient was predicted to be a responder but likely to have an immune-related adverse event (irAE) (FIG. 11), FS peptide signature analysis could be integrated into the treatment plan. irAE are generally graded from 1-4. Grades 3 and 4 are considered serious and can require immunosuppression treatment. Patients with irAE are just as likely to have a positive response to treatment. Occurrence of Grade 3 or 4 event can prohibit the patient from further checkpoint therapy. Therefore, knowing ahead of time which patients are more likely to have an event would allow closer monitoring to pre-empt a 3 or 4 event. The irAE patients in FIG. 11 experienced grade 2 or higher events (e.g., hypothyroidism, diarrhea, elevated ALT/AST (hepatotoxicity), colitis, diabetes, rash, fatigue). It is of note that, even though they suffered from a variety of events, they had a common predictive signature.

What is claimed is:

1. A method of treating a subject with an immunotherapeutic, the method comprising the steps of:
contacting a biological sample comprising antibodies from a subject to a frameshift array comprising a plurality of tumor-associated frameshift peptides, wherein the plurality of tumor-associated frameshift peptides comprise frameshift peptides derived from indels arising during RNA transcription or from mis-splicing of exons;
measuring binding of antibodies having affinity to one or more of the tumor-associated frameshift peptides in the contacted biological sample;
for each of the plurality of tumor-associated frameshift peptides, quantifying levels of binding of the antibodies having affinity to one or more of the tumor-associated frameshift peptides to form a frameshift signature of the subject,
wherein the quantified levels of binding are indicative of whether the subject is likely to experience an immune-related adverse event in response to treatment of an immunotherapeutic; and
treating the subject with the immunotherapeutic.

2. The method of claim 1, wherein the immunotherapeutic is selected from the group consisting of a cytotoxic T-lymphocyte associated protein 4 (CTLA-4) inhibitor, a programmed death-ligand 1 (PD-L1) inhibitor, and a programmed death-1 (PD-1) inhibitor.

3. The method of claim 1, wherein the biological sample is a blood or tissue sample.

4. The method of claim 3, wherein the blood sample is a peripheral blood sample.

5. The method of claim 1, wherein the subject is a mammal.

6. The method of claim 5, wherein the mammal is a human.

7. The method of claim 5, wherein the mammal is a canine.

8. The method of claim 1, further comprising creating a record indicating the subject is likely to experience an adverse event in response to the immunotherapeutic treatment based on the frameshift signature.

9. The method of claim 8, wherein said record is created on a computer readable medium.

10. The method of claim 1, wherein the tumor-associated frameshift peptides are 8-60 amino acids in length.

11. The method of claim 1, wherein the tumor-associated frameshift peptides are 9-25 amino acids in length.

12. The method of claim 1, wherein the binding of antibodies having affinity to one or more of the tumor-associated frameshift peptides comprises cognate binding.

13. The method of claim 1, wherein the tumor-associated frameshift peptides comprise a frameshift peptide longer than 15 amino acids represented by 2 or more tumor-associated frameshift peptides on the frameshift array.

14. The method of claim 1, wherein the frameshift array comprises 100,000 to 500,000 tumor-associated frameshift peptides.

15. The method of claim 1, wherein the step of measuring, with a device, binding of antibodies comprises detecting a fluorescent label.

16. The method of claim 15, wherein the step of electrically quantifying levels of binding comprises determining a quantitative amount of fluorescence.

17. The method of claim 1, wherein the frameshift signature comprises a quantitative measurement of binding of the antibodies to the tumor-associated frameshift peptides.

18. A method of modifying a treatment with an immunotherapeutic of a subject, comprising:
contacting a biological sample comprising antibodies from a subject to a frameshift array comprising a plurality of tumor-associated frameshift peptides,
wherein the tumor-associated frameshift peptides comprise a frameshift peptide longer than 15 amino acids represented by 2 or more tumor-associated frameshift peptides on the frameshift array, and
wherein the tumor-associated frameshift peptides comprise frameshift peptides derived from indels arising during RNA transcription or from mis-splicing of exons;
measuring binding of antibodies having affinity to one or more of the tumor-associated frameshift peptides in the contacted biological sample by detecting a fluorescent label;
for each of the plurality of tumor-associated frameshift peptides, quantifying levels of binding of the antibodies having affinity to one or more of the tumor-associated frameshift peptides by determining a quantitative amount of fluorescence; and
modifying a treatment of the subject with the immunotherapeutic.

19. The method of claim 18, wherein the quantified levels of binding are indicative of whether the subject is likely to experience an immune-related adverse event in response to treatment with an immunotherapeutic.

* * * * *